US011559231B2

(12) United States Patent
Dabrowska

(10) Patent No.: US 11,559,231 B2
(45) Date of Patent: Jan. 24, 2023

(54) SYSTEM AND METHOD FOR DETERMINING A DISCRIMINATION INDEX FOR FEAR-POTENTIATED STARTLE

(71) Applicant: Rosalind Franklin University of Medicine and Science, North Chicago, IL (US)

(72) Inventor: Joanna Dabrowska, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 326 days.

(21) Appl. No.: 16/414,951

(22) Filed: May 17, 2019

(65) Prior Publication Data

US 2019/0357832 A1  Nov. 28, 2019

Related U.S. Application Data

(60) Provisional application No. 62/720,620, filed on Aug. 21, 2018, provisional application No. 62/673,447, filed on May 18, 2018.

(51) Int. Cl.
| | | |
|---|---|---|
| *A61B 5/16* | (2006.01) | |
| *A61B 5/00* | (2006.01) | |
| *A61B 5/145* | (2006.01) | |
| *A61K 38/095* | (2019.01) | |
| *A61K 9/00* | (2006.01) | |
| *A61P 25/22* | (2006.01) | |

(52) U.S. Cl.
CPC .......... *A61B 5/165* (2013.01); *A61B 5/14528* (2013.01); *A61B 5/16* (2013.01); *A61B 5/162* (2013.01); *A61B 5/4848* (2013.01); *A61B 5/4884* (2013.01); *A61B 5/7246* (2013.01); *A61K 9/0043* (2013.01); *A61K 38/095* (2019.01); *A61P 25/22* (2018.01)

(58) Field of Classification Search
None
See application file for complete search history.

(56) References Cited

U.S. PATENT DOCUMENTS

2007/0032410 A1* 2/2007 Quay .................... A61K 9/0043
514/183

OTHER PUBLICATIONS

Delgado et al. (International Journal of Psychophysiology 74 (2009) 280-287) (Year: 2009).*
Acheson et al. (Psychopharmacology (2013) 229:199-208) (Year: 2013).*
Norrholm et al. (Learn Mem. 2006 ; 13(6): 681-685) (Year: 2006).*
Acheson, D., et al., "The Effect of Intranasal Oxytocin Treatment on Conditioned Fear Extinction and Recall in a Healthy Human Sample", Psychopharmacology, 2013, vol. 229, pp. 199-208, doi:10.1007/s00213-013-3099-4.
Ayers, L.W., et al., "Oxytocin Reduces Background Anxiety in a Fear-Potentiated Startle Paradigm: Peripheral vs Central Administration", Neuropsychopharmacology, Nov. 2011, vol. 36(12), pp. 2488-2497, doi:10.1038/npp.2011.138, Epub Jul. 27, 2011.
Ayers, L., et al., "Effects of Oxytocin on Background Anxiety in Rats with High or Low Baseline Startle", Psychopharmacology (Berl), Jun. 2016, vol. 233(11), pp. 2165-2172, doi:10.1007/s00213-016-4267-0, Epub Mar. 23, 2016.
Bale, T.L., et al., "CNS Region-Specific Oxytocin Receptor Expression: Importance in Regulation of Anxiety and Sex Behavior", Journal of Neuroscience, Apr. 2001, vol. 21(7), pp. 2546-2552.
Bosch, O.J., et al., "Release of Oxytocin in the Hypothalamic Paraventricular Nucleus, but not Central Amygdala or Lateral Septum in Lactating Residents and Virgin Intruders during Maternal Defence", Neuroscience, 2004, vol. 124(2), pp. 439-448. (Abstract only).
Bosch, O.J., et al., "Oxytocin in the Nucleus Accumbens Shell Reverses CRFR2-Evoked Passive Stress-Coping After Partner Loss in Monogamous Male Prairie Voles", Psychoneuroendocrinology, Feb. 2016, vol. 64, pp. 66-78, doi:10.1016/j.psyneuen.2015.11.011.
Dabrowska, J., et al., "Reactivity of 5-HT1A Receptor in Adult Rats after Neonatal Noradrenergic Neurons' Lesion-Implications for Antidepressant-Like Action", Brain Research, Nov. 2008, vol. 1239, pp. 66-76, doi:10.1016/j.brainres.2008.08.054, Epub Aug. 29, 2008. (Abstract only).
Dabrowska, J., et al., "Neuroanatomical Evidence for Reciprocal Regulation of Thecorticotrophin-Releasing Factor and Oxytocin Systems in the Hypothalamus and the Bed Nucleus of the Stria Terminalis of the Rat: Implications for Balancing Stress and Affect", Psychoneuroendocrinology, Oct. 2011, vol. 36(9), pp. 1312-1326, doi:10.1016/j.psyneuen.2011.03.003.
Dabrowska, J., et al., "Striatal Enriched Protein Tyrosine Phosphatase-Steps Toward Understanding Chronic Stress Induced Activation of Corticotrophin Releasing Factor Neurons in the Rat Bed Nucleus of the Stria Terminalis", Biological Psychiatry, Dec. 2013, vol. 74(11), pp. 817-826, doi:10.1016/j.biopsych.2013.07.032.

(Continued)

*Primary Examiner* — Sergio Coffa
(74) *Attorney, Agent, or Firm* — McDonnell Boehnen Hulbert & Berghoff LLP

(57) ABSTRACT

A method and system is provided for determining a discrimination index in a subject that may be suffering from or at risk for a stress-induced psychiatric disorder. The discrimination index may be equal to a ratio of a subject's cued fear response and non-cued fear response measured during a fear-potentiated startle (FPS) paradigm. Such a value may allow a physician or researcher to quantify how well a subject discriminates between signaled (cued) fear and un-signaled (non-cued) fear, which may be a biomarker for psychiatric disorders like post-traumatic stress disorder, panic disorder, phobias, and/or generalized anxiety disorder. The determined discrimination index may provide a standardized way of diagnosing and evaluating mental illnesses, more uniform treatment of patients, and/or more precise monitoring and evaluation of treatment efficacy.

12 Claims, 13 Drawing Sheets

(56) References Cited

OTHER PUBLICATIONS

Daniel, S.E., et al., "Stress Modulation of Opposing Circuits in the Bed Nucleus of the Stria Terminalis", Neuropsychopharmacologycology, 2016, vol. 41, pp. 103-125.
Davis, M., et al., "Phasic vs Sustained Fear in Rats and Humans: Role of the Extended Amygdala in Fear vs Anxiety", Neuropsychopharmacology, 2010, vol. 35, pp. 105-135.
De Bundel, D., et al., "Dopamine D2 Receptors Gate Generalization of Conditioned Threat Responses through mTORC1 Signaling in the Extended Amygdala", Molecular Psychiatry, Nov. 2016, vol. 21(11), pp. 1545-1553, doi:10.1038/mp.2015.210.
Dumais, K.M., et al., "Sex Differences in Oxytocin Receptor Binding in Forebrain Regions: Correlations with Social Interest in Brain Region-and Sex Specific Ways", Hormones and Behavior, Sep. 2013, vol. 64(4), pp. 693-701, doi:10.1016/j.yhbeh.2013.08.012, Epub Sep. 18, 2013. (Abstract only).
Dumais, K.M., et al., "Involvement of the Oxytocin System in the Bed Nucleus of the Stria Terminalis in the Sex-Specific Regulation of Social Recognition", Psychoneuroendocrinology, Feb. 2016, vol. 64, pp. 79-88, doi:10.1016/j.psyneuen.2015.11.007.
Duvarci, S., et al., "The Bed Nucleus of the Stria Terminalis Mediates Inter Individual Variations in Anxiety and Fear", Journal of Neuroscience, Aug. 2009, vol. 29(33), pp. 10357-10361, doi:10.1523/JNEUROSCI.2119-09.2009.
Ebner, K., et al., "A Single Social Defeat Experience Selectively Stimulates the Release of Oxytocin, but not Vasopressin, Within the Septal Brain Area of Male Rats", Brain Research, Jul. 2000, vol. 872(1-2), pp. 87-92. (Abstract only).
Ebner, K., et al., "Release of Oxytocin in the Rat Central Amygdala Modulates Stress-Coping Behavior and the Release of Excitatory Amino Acids", Neuropsychopharmacology, Feb. 2005, vol. 30(2), pp. 223-230. (Abstract only).
Ellenbogen, M.A., et al., "Intranasal Oxytocin Attenuates the Human Acoustic Startle Response Independent of Emotional Modulation", Psychophysiology, Nov. 2014, vol. 51(11), pp. 1169-1177, doi:10.1111/psyp.12263, Epub Aug. 1, 2014. (Abstract only).
Fam, J, et al., "Oxytocin Receptor Activation in the Basolateral Complex of the Amygdala Enhances Discrimination Between Discrete Cues and Promotes Configural Processing of Cues", Psychoneuroendocrinology, Oct. 2018, vol. 96, pp. 84-92, doi:10.1016/j.psyneuen.2018.06.006, Epub Jun. 15, 2018. (Abstract only).
Fani, N., et al., "Fear-Potentiated Startle During Extinction is Associated with White Matter Microstructure and Functional Connectivity", Cortex, Mar. 2015, vol. 64, pp. 249-259, doi:10.1016/j.cortex.2014.11.006.
Gewirtz, J.C., et al., "Lesions of the Bed Nucleus of the Stria Terminalis Block Sensitization of the Acoustic Startle Reflex Produced by Repeated Stress, but not Fear Potentiated Startle", Progress in Neuro-Psychopharmacology & Biological Psychiatry, May 1998, vol. 22(4), pp. 625-648. (Abstract only).
Glover, E.M., et al., "Tools for Translational Neuroscience: PTSD is Associated with Heightened Fear Responses Using Acoustic Startle but not Skin Conductance Measures", Depression and Anxiety, Dec. 21, 2011, vol. 28(12), pp. 1058-1066, doi:10.1002/da.20880.
Goode, T.D., et al., "Role of the Bed Nucleus of the Stria Terminalis in Aversive Learning and Memory", Learning & Memory, Aug. 2017, vol. 24(9), pp. 480-491, doi:10.1101/lm.044206.116, Print Sep. 2017.
Grillon, C., et al., "Increased Anxiety During Anticipation of Unpredictable Aversive Stimuli in Post Traumatic Stress Disorder but not in Generalized Axnxiety Disorder", Biological Psychiatry, Jul. 2009, vol. 66(1), pp. 47-53, doi:10.1016/j.biopsych.2008.12.028.
Gungor, N.Z., et al., "Functional Heterogeneity in the Bed Nucleus of the Stria Terminalis", Journal of Neuroscience, Aug. 2016, vol. 36(31), pp. 8038-8049.
Guzman, Y.F., et al., "Fear-Enhancing Effects of Septal Oxytocin Receptors", Nature Neuroscience, Sep. 2013, vol. 16(9), pp. 1185-1187, doi:10.1038/nn.3465.
Hascup, E.R., et al., "Histological Studies of the Effects of Chronic Implantation of Ceramic-Based Microelectrode Arrays and Microdialysis Probes in Rat Prefrontal Cortex", Brain Research, Sep. 2009, vol. 1291, pp. 12-20, doi:10.1016/j.brainres.2009.06.084.
Haufler, D., et al., "Neuronal Correlates of Fear Conditioning in the Bed Nucleus of the Stria Terminalis", Learning & Memory, Oct. 2013, vol. 20(11), pp. 633-641, doi:10.1101/lm.031799.113.
Hitchcock, J.M., et al., "Efferent Pathway of the Amygdala Involved in Conditioned Fear as Measured with the Fear-Potentiated Startle Paradigm", Behavioral Neuroscience, Dec. 1991, vol. 105(6), pp. 826-842. (Abstract only).
Janeček, M., et al., "Oxytocin Facilitates Adaptive Fear and Attenuates Anxiety Responses in Animal Models and Human Studies-Potential Interaction with the Corticotropin-Releasing Factor (CRF) System in the Bed Nucleus of the Stria Terminalis (BNST)", Cell and Tissue Research, Jul. 2018, vol. 353(3), pp. 1-32, doi:10.1007/s00441-018-2889-8.
Knobloch, H.S., et al., "Evoked Axonal Oxytocin Release in the Central Amygdala Attenuates Fear Response", Neuron, Feb. 2012, vol. 73(3), pp. 553-566, doi:10.1016/j.neuron.2011.11.030. (Abstract only).
Lahoud, N., et al., "Oxytocinergic Manipulations in Corticolimbic Circuit Differentially Affect Fear Acquisition and Extinction", Psychoneuroendocrinology, Oct. 2013, vol. 38(10), pp. 2184-2195, doi:10.1016/j.psyneuen.2013.04.006. (Abstract only).
Landgraf, R., et al., "Vasopressin and Oxytocin Release Within the Brain: A Dynamic Concept of Multiple and Variable Modes of Neuropeptide Communication", Frontiers in Neuroendocrinology, Sep.-Dec. 2004, vol. 25(3-4), pp. 150-176. (Abstract only).
Lange, M.D., et al., "Cannabinoid CB1 Receptors Indistinct Circuits of the Extended Amygdala Determine Fear Responsiveness to Unpredictable Threat", Molecular Psychiatry, Oct. 2017, vol. 22(10), pp. 1422-1430, doi:10.1038/mp.2016.156, Epub Oct. 4, 2016. (Abstract only).
Lebow, M., et al., "Susceptibility to PTSD-like Behavior is Mediated by Corticotropin-Releasing Factor Receptor Type 2 Levels in the Bed Nucleus of the Stria Terminalis", Journal of Neuroscience, May 2012, vol. 32(20), pp. 6906-6916, doi: 10.1523/JNEUROSCI.4012-11.2012.
LeDoux, J.E., et al., "Different Projections of the Central Amygdaloid Nucleus Mediate Autonomic and Behavioral Correlates of Conditioned Fear", Journal of Neuroscience, Jul. 1988, vol. 8(7), pp. 2517-2529.
Luyck, K., et al., "Electrolytic Post-Training Lesions of the Bed Nucleus of the Stria Terminalis Block Startle Potentiation in a Cued Fear Conditioning Procedure", Brain Structure & Function, May 2018, vol. 223(4), pp. 1839-1848, doi:10.1007/s00429-017-1591-z, Epub Dec. 16, 2017. (Abstract only).
Manning, M., et al., "Oxytocin and Vasopressin Agonists and Antagonists as Research Tools and Potential Therapeutics", Journal of Neuroendocrinology, Apr. 2012, vol. 24, pp. 609-628, doi:10.1111/j.1365-2826.2012.02303.x.
Marcinkiewcz, C.A., et al., "Serotonin Engages an Anxiety and Fear-Promoting Circuit in the Extended Amygdala", Nature, Sep. 2016, vol. 537(7618), pp. 97-101, doi:10.1038/nature19318, Epub Aug. 24, 2016.
Martinon, D., et al., "Oxytocin Receptors in the Dorsolateral Bed Nucleus of the Stria Terminalis (BNST) Bias Fear Learning Toward Temporally Predictable Cued Fear", Translational Psychiatry, Apr. 2019, vol. 9(1):140, pp. 1-13, doi:10.1038/s41398-019-0474-x.
Martinon, D., et al., "Corticotropin-Releasing Factor Receptors Modulate Oxytocin Release in the Dorsolateral Bed Nucleus of the Stria Terminalis (BNST) in Male Rats", Frontiers in Neuroscience, Mar. 2018, vol. 12, Article 183, pp. 1-12, doi:10.3389/fnins.2018.00183, eCollection 2018.
Missig, G.,et al., "Oxytocin Reduces Background Anxiety in a Fear-Potentiated Startle Paradigm", Neuropsychopharmacology, Dec. 2010, vol. 35(13), pp. 2607-2616, doi: 10.1038/npp.2010.155, Epub Sep. 15, 2010.

(56) References Cited

OTHER PUBLICATIONS

Moaddab, M., et al., "Oxytocin Receptor Neurotransmission in the Dorsolateral Bed Nucleus of the Stria Terminalis Facilitates the Acquisition of Cued Fear in the Fear Potentiated Startle Paradigm in Rats", Neuropharmacology, Jul. 2017, vol. 121, pp. 130-139, doi:10.1016/j.neuropharm.2017.04.039, Epub Apr. 26, 2017.

Nasanbuyan, N., et al., "Oxytocin-Oxytocin Receptor Systems Facilitate Social Defeat Posture in Male Mice", Endocrinology, Feb. 2018, vol. 159(2), pp. 763-775, doi:10.1210/en.2017-00606.

Neumann, I., et al., "Oxytocin and Vasopressin Release Within the Supraoptic and Paraventricular Nuclei of Pregnant, Parturient and Lactating Rats: A Microdialysis Study", Neuroscience, Mar. 1993, vol. 53(1), pp. 65-75. (Abstract only).

Neumann, I.D., et al., "Stimuli and Consequences of Dendritic Release of Oxytocin Within the Brain", Biochem. Soc. Trans., Nov. 2007, vol. 35(Pt. 5), pp. 1252-1257. (Abstract only).

Neumann, I.D., et al., "Oxytocin in General Anxiety and Social Fear: A Translational Approach", Biological Psychiatry, Feb. 2016, vol. 79(3), pp. 213-221, doi:10.1016/j.biopsych.2015.06.004, Epub Jun. 10, 2015. (Abstract only).

Nishioka, T., et al, "Stress Increases Oxytocin Release Within the Hypothalamic Paraventricular Nucleus", Brain Research, Jan. 1998, vol. 781(1-2), pp. 57-61. (Abstract only).

Paxinos, G., et al., "The Rat Brain In Stereotaxic Coordinates", 6th Edition, Oxford, UK: Academic Press, Elsevier, 2007. (Abstract/Synopsis only).

Pelrine, E., et al., "5-HT2C Receptors in the BNST are Necessary for the Enhancement of Fear Learning by Selective Serotonin Reuptake Inhibitors", Neurobiology of Learning and Memory, Dec. 2016, vol. 136, pp. 189-195, doi:10.1016/j.nlm.2016.10.008.

Ravinder, S., et al., "A role for the Extended Amygdala in the Fear-Enhancing Effects of Acute Selective Serotonin Reuptake Inhibitor Treatment", Translational Psychiatry, Jan. 2013, vol. 3(1):e209, pp. 1-11, doi:10.1038/tp.2012.137.

Ring, R.H., et al, "Anxiolytic-Like Activity of Oxytocin in Male Mice: Behavioral and Autonomic Evidence, Therapeutic Implications", Psychopharmacology (Berl), Apr. 2006, vol. 185(2), pp. 218-225, Epub Jan. 18, 2006. (Abstract only).

Robinson, D.A., et al, "Oxytocin Mediates Stress-Induced Analgesia in Adult Mice", The Journal of Physiology, Apr. 2002, vol. 540.2, pp. 593-606.

Ross, H.E., et al., "Characterization of the Oxytocin System Regulating Affiliative Behavior in Female Prairie Voles", Neuroscience, Sep. 2009, vol. 162(4), pp. 892-903, doi:10.1016/j.neuroscience.2009.05.055.

Sullivan, G.M., et al., "Lesions in the Bed Nucleus of the Stria Terminalis Disrupt Corticosterone and Freezing Responses Elicited by a Contextual but not by a Specific Cue-Conditioned Fear Stimulus", Neuroscience, Jun. 2004, vol. 128(1), pp. 7-14, doi:10.1016/j.neuroscience.2004.06.015. (Abstract only).

Toth, I., et al., "Central Administration of Oxytocin Receptor Ligands Affects Cued Fear Extinction in Rats and Mice in a Timepoint-Dependent Manner", Psychopharmacology (Berl), Sep. 2012, vol. 223(2), pp. 149-158, doi:10.1007/s00213-012-2702-4, Epub Apr. 20, 2012. (Abstract only).

Tribollet, E., et al. "Oxytocin Receptors in the Central Nervous System. Distribution, Development, and Species Differences", Annals of the New York Academy of Sciences, Jun. 1992, vol. 652, pp. 29-38. (Abstract only).

Veinante, P., et al., "Distribution of Oxytocin- and Vasopressin-Binding Sites in the Rat Extended Amygdala: A Histoautoradiographic Study", Journal of Comparative Neurology, Jul. 1997, vol. 383(3), pp. 305-325. (Abstract only).

Walker, D.L., et al., "The Role of Amygdala Glutamate Receptors in Fear Learning, Fear Potentiated Startle, and Extinction", Pharmacology, Biochemistry, and Behavior, Mar. 2002, vol. 71(3), pp. 379-392. (Abstract only).

Walker, D.L., et al., "Differential Effects of the CRF-R1 Antagonist GSK876008 on Fear-Potentiated, Light- and CRF-Enhanced Startle Suggest Preferential Involvement in Sustained versus Phasic Threat Responses", Neuropsychopharmacology, May 2009, vol. 34(6), pp. 1533-1542, doi:10.1038/npp.2008.210.

Wilensky, A.E., et al., "Rethinking the Fear Circuit: the Central Nucleus of the amygdala is Required for the Acquisition, Consolidation, and Expression of Pavlovian Fear Conditioning", Journal of Neuroscience, Nov. 2006, vol. 26(48), pp. 12387-12396, doi:10.1523/JNEUROSCI.4316-06.2006.

Wotjak, C.T., et al., "Forced Swimming Stimulates the Expression of Vasopressin and Oxytocin in Magnocellular Neurons of the Rat Hypothalamic Paraventricular Nucleus", European Journal of Neuroscience, Jun. 2001, vol. 13(12), pp. 2273-2281. (Abstract only).

Zhu, L., et al., "Involvement of Medullary A2 Noradrenergic Neurons in the Activation of Oxytocin Neurons after Conditioned Fear Stimuli", European Journal of Neuroscience, Dec. 2002, vol. 16(11), pp. 2186-2198. (Abstract only).

Bosch, O.J. and Young, L.J., et al., "Oxytocin and Social Relationships: From Attachment to Bond Disruption", Curr. Top Behav. Neurosci., 2018, vol. 35, pp. 97-117.

Han, J.S., et al., "Dual Actions of Vasopressin and Oxytocin in Regulation of Water Permeability in Terminal Collecting Duct", Laboratory of Kidney and Electrolyte Metabolism, National Heart, Lung, and Blood Institute, National Institutes of Health, 1993, pp. F26-F34.

Caldeyro-Barcia, R., et al., "Oxytocin and Contractility of the Pregnant Human Uterus", Annals New York Academy of Sciences, 1959, pp. 813-830.

Dunsmoor, J.E., et al., "Fear Generalization and Anxiety: Behavioral and Neural Mechanisms", Biological Psychiatry, Sep. 1, 2015, vol. 78, pp. 336-343.

Liddell, B.J., et al., "A Direct Brainstem-Amygdala-Cortical 'Alarm' System for Subliminal Signals of Fear", NeuroImage, 2005, vol. 24, pp. 235-243.

Lissek, S., et al., "Generalized Anxiety Disorder Is Associated With Overgeneralization of Classically Conditioned Fear", Biol. Psychiatry, 2014, vol. 75, pp. 909-915.

LoBue, V., et al., "Detecting the Snake in the Grass", Psychological Science, 2007, vol. 19(3), pp. 284-289.

LoBue, V., "More Than Just Another Face in the Crowd: Superior Detection of Threatening Facial Expressions in Children and Adults", Developmental Science, 2009, vol. 12(2), pp. 305-313.

Pedersen, C.A., et al., "Oxytocin Activation of Maternal Behavior in the Rat", Annals New York Academy of Sciences, 1992, pp. 58-69.

Reinders, A.A.T.S., et al., "Detecting Fearful and Neutral Faces: BOLD Latency Differences in Amygdala-Hippocampal Junction", NeuroImage, 2006, vol. 33, pp. 805-814.

Walker, D.L., et al., "Selective Participation of the Bed Nucleus of the Stria Terminalis and CRF in Sustained Anxiety-Like Versus Phasic Fear-Like Responses", Progress in Neuro-Psychopharmacology & Biological Psychiatry, 2009, vol. 33, pp. 1291-1308.

Marvar, P.J., et al., "Limbic Neuropeptidergic Modulators of Emotion and Their Therapeutic Potential for Anxiety and Post-Traumatic Stress Disorder", The Journal of Neuroscience, Feb. 3, 2021, vol. 41(5), pp. 901-910.

Verbalis, J.G., et al., "Central Oxytocin Inhibition of Food and Salt Ingestion: a Mechanism for Intake Regulation of Solute Homeostasis", Regulatory Peptides, 1993, vol. 45, pp. 149-154.

Olivera-Pasilio, V. and Dabrowska, J., "Oxytocin Promotes Accurate Fear Discrimination and Adaptive Defensive Behaviors", Frontiers in Neuroscience, Sep. 2020, vol. 14, Article 583878, pp. 1-12.

Nickerson, K., et al., "Oxytocin and Milk Ejection", Am. J. Obst. & Gynec., May 1954, vol. 67(5), pp. 1028-1034.

Sofroniew, M.V., "Morphology of Vasopressin and Oxytocin Neurones and their Central and Vascular Projections", The Neurohypophysis: Structure, Function and Control, Progress in Brain Research, 1983, vol. 60, pp. 101-114.

Swanson, L.W., et al., "Hypothalamic Integration: Organization of the Paraventricular and Supraoptic Nuclei", Ann. Rev. Neurosci., 1983, vol. 6, pp. 269-324.

\* cited by examiner

A. OT release in the BNST via in vivo microdialysis

B. Activation of OT neurons in the hypothalamus

C. OTR transmission in the BNST – fear modulation in the FPS

| CONDITION OT pg/100 µl MEAN ± SEM | Baseline | 30 min | 60 min | 90 min | 120 min | 150 min |
|---|---|---|---|---|---|---|
| CTRL FPS (n = 7) | 1.19 ± 0.05 | 1.16 ± 0.08 | 1.18 ± 0.04 | 1.21 ± 0.11 | 1.18 ± 0.04 | 1.15 ± 0.09 |
| SHOCK (n = 6) | 1.20 ± 0.12 | 1.22 ± 0.19 | 1.18 ± 0.18 | 1.22 ± 0.15 | 1.26 ± 0.15 | 1.19 ± 0.16 |
| SHOCK + CUE (n = 8) | 1.06 ± 0.06 | 1.41 ± 0.14 | 1.29 ± 0.11 | 1.12 ± 0.08 | 1.15 ± 0.07 | 1.08 ± 0.09 |
| CTRL FS (n = 10) | 1.06 ± 0.08 | 1.18 ± 0.19 | 0.92 ± 0.04 | 0.96 ± 0.12 | 0.92 ± 0.06 | 0.90 ± 0.13 |
| FS (n = 8) | 1.01 ± 0.10 | 1.11 ± 0.15 | 0.93 ± 0.11 | 0.93 ± 0.10 | 1.07 ± 0.15 | 0.89 ± 0.11 |
| CTRL SI (n = 8) | 1.02 ± 0.04 | 0.90 ± 0.07 | 0.99 ± 0.09 | 0.89 ± 0.08 | 0.95 ± 0.11 | 0.82 ± 0.05 |
| SI (n = 6) | 1.06 ± 0.08 | 0.99 ± 0.10 | 1.11 ± 0.09 | 0.94 ± 0.06 | 1.07 ± 0.11 | 1.09 ± 0.09 |

Figure 7

|  |  | All AREAS | AREA 1 | AREA 2 | AREA 3 |
|---|---|---|---|---|---|
| PVN | Control | 5.43 ± 2.11 | 4.92 ± 3.76 | 4.61 ± 3.11 | 8.90 ± 5.49 |
|  | Shock alone | 15.69 ± 2.73 | 17.21 ± 5.67 | 19.54 ± 10.79 | 7.13 ± 3.73 |
|  | Shock and cue | 9.64 ± 2.33 | 11.46 ± 5.27 | 6.62 ± 2.85 | 11.24 ± 8.73 |
| SON | Control | 3.81 ± 0.79 | 5.60 ± 2.08 | 1.78 ± 0.96 | N/A |
|  | Shock alone | 22.03 ± 2.38 | 24.69 ± 5.09 | 28.12 ± 5.05 | N/A |
|  | Shock and cue | 11.91 ± 1.60 | 10.40 ± 3.01 | 11.99 ± 2.84 | N/A |
| AN | Control | 4.69 ± 1.57 | 8.29 ± 7.66 | 2.57 ± 0.833 | 3.58 ± 2.90 |
|  | Shock alone | 18.95 ± 2.14 | 12.79 ± 4.46 | 15.29 ± 4.60 | 24.69 ± 7.023 |
|  | Shock and cue | 13.58 ± 2.75 | 10.52 ± 6.24 | 12.83 ± 4.32 | 26.24 ± 8.06 |

Figure 8

SYSTEM AND METHOD FOR DETERMINING A DISCRIMINATION INDEX FOR FEAR-POTENTIATED STARTLE

CROSS-REFERENCE TO RELATED APPLICATION

This application claims the benefit of priority to U.S. Provisional Patent Application No. 62/673,447, filed May 18, 2018, and U.S. Provisional Patent Application No. 62/720,620, filed Aug. 21, 2018, both which is hereby incorporated by reference in its entirety.

STATEMENT REGARDING FEDERALLY SPONSORED RESEARCH OR DEVELOPMENT

This invention was made with government support under R01 MH113007 awarded by the National Institutes of Health (NIH). The government has certain rights in the invention.

BACKGROUND

Oxytocin (OT) is a peptide hormone and a neuromodulator produced by neurons of the paraventricular (PVN), supraoptic (SON), as well as accessory nuclei (AN) of the hypothalamus (Sofroniew, 1983; Swanson and Sawchenko, 1983). As a hormone, OT is released from the posterior pituitary into general blood circulation, where it mediates a variety of pivotal physiological processes, including uterine contractions during labor and milk ejection reflex (Nickerson et al., 1954; Caldeyro-Barcia and Poseiro, 1959). In addition, together with arginine vasopressin (AVP), OT is a master regulator of water/electrolyte balance (Han et al., 1993; Verbalis et al., 1993). In the central nervous system (CNS), this nine amino-acid neuropeptide has been shown to produce powerful effects on a wide array of social behaviors, including but not limited to, pair bond formation, social recognition, and the onset of maternal behavior (Pedersen et al., 1992; Bosch and Young, 2017). Furthermore, in both female and male rats, OT neurons from the hypothalamus send considerable projections to the CNS, including many brain structures that are critical for the modulation of fear and anxiety-like behaviors (Dabrowska et al., 2011; Knobloch et al., 2012).

Fear response allows accurate and rapid threat detection that facilitates survival (Liddell et al., 2005; Reinders et al., 2006). Hence, as observed in infants, children, and adults, humans are innately biased toward rapid detection of threatening vs. non-threatening stimuli (Lobue and DeLoache, 2008) and fearful vs. happy or neutral facial expressions (LoBue, 2009). In contrast to fear, anxiety occurs in the absence of a threat stimulus or in anticipation of a threat, hence anxiety can be defined as a sustained and maladaptive response to diffuse, less specific, unpredictable or un-signaled threats (Davis et al., 2010; Goode and Maren, 2017). Anxiety can occur as an over-generalization of learned fear, inability to extinguish fear, and inability to discriminate between a threat and safety (Lissek et al., 2014; Dunsmoor and Paz, 2015). These characteristics lay the foundation of stress-induced psychiatric disorders including post-traumatic stress disorder (PTSD), panic disorder, and generalized anxiety-disorder (GAD).

To determine a subject's susceptibility to a stress disorder, a subject's physiological reaction to threatening and non-threatening stimuli can be evaluated as part of a fear-potentiated startle (FPS) paradigm. During such an experimental protocol, various stimuli can be presented to a subject, and the reflexive physiological response (i.e., the startle response or startle reflex) to each stimulus can be measured. In some cases, the inability to discriminate between a conditioned fear-inducing stimulus (i.e., a signaled threat) and a non-fear-inducing stimulus (i.e., a non-signaled threat) can indicate that a subject may be at risk for a psychiatric stress disorder. However, currently there is no standardized methodology or behavioral biomarker for determining stress disorder susceptibility, diagnosis, and/or progression from FPS results. Accordingly, there is a need for a method of evaluating the development of stress disorders in a patient in a way that is quantitative, measurable, and repeatable.

SUMMARY

The present disclosure generally relates to a system for determining a discrimination index (DI), which may be implemented when evaluating a subject's ability to distinguish threatening from safe stimuli during a fear-potentiated startle (FPS) paradigm. In this disclosure, the terms "subject" and "patient" may be used interchangeably. In some embodiments, the "subject" could refer to a human or nonhuman animal, e.g., mammals and non-mammals, such as nonhuman primates, sheep, dogs, cats, mice, rats, amphibians, reptiles, and the like. In some embodiments, the subject is a human patient that being evaluated for a stress-induced psychiatric disorder. In a particular embodiment, the subject is a human patient being evaluated for post-traumatic stress disorder (PTSD).

In a first implementation, a method is provided. The method includes providing a cued fear response value of a subject and providing a non-cued fear response value of the subject. The method further includes determining a discrimination index. The discrimination index is equal to a ratio of the cued fear response value to the non-cued fear response value. The method additionally includes administering a therapy to the subject if the discrimination index is less than 1 or equal to 1.

In some embodiments, the therapy is sufficient to increase the discrimination index to greater than 1. In further embodiments, the therapy comprises a pharmaceutical agent or an evidence-based psychotherapy. In additional embodiments, the pharmaceutical agent comprises oxytocin. In yet further embodiments, administering the therapy to the subject comprises administering intranasal oxytocin.

In a second implementation, a method is provided. The method includes administering a therapy to a subject suffering from a stress-induced psychiatric disorder. The method further includes providing a cued fear response value of the subject and providing a non-cued fear response value of the subject. The method additionally includes determining a discrimination index. The discrimination index is equal to a ratio of the cued fear response value to the non-cued fear response value. The method additionally includes determining an efficacy of the therapy based on at least the determined discrimination index.

In some embodiments, the stress-induced psychiatric disorder includes at least one of post-traumatic stress disorder (PTSD), panic disorder, a phobia, or generalized anxiety disorder (GAD). In further embodiments, determining the efficacy of the therapy comprises determining that the therapy is effective if the discrimination index is greater than 1, and wherein determining the efficacy of the therapy comprises determining that the therapy is not effective if the discrimination index is equal to or less than 1. In still further embodiment, determining the efficacy of the therapy comprises determining that the therapy is effective if the discrimination index is progressively increasing to 1 or more, and wherein determining the efficacy of the therapy comprises determining that the therapy is not effective if the discrimination index is progressively decreasing to 1 or less. In some embodiments, the method further comprises if the discrimination index is less than or equal to 1, then administering an adjusted amount of the therapy to the subject such that the adjusted amount of the therapy is sufficient to increase the discrimination index to greater than 1.

In a third implementation, a method is provided. The method includes providing a cued fear response value of a subject and providing a non-cued fear response value of a subject. The method further includes determining a discrimination index. The discrimination index is equal to a ratio of the cued fear response value to the non-cued fear response value. The method additionally includes performing a diagnostic process. The diagnostic process comprises diagnosing a presence of or susceptibility to a stress-induced psychiatric disorder if the discrimination index is less than or equal to 1; and diagnosing an absence of or resilience to a stress-induced psychiatric disorder if the discrimination index is greater than 1.

In some embodiments, the stress-induced psychiatric disorder includes at least one of post-traumatic stress disorder (PTSD), panic disorder, a phobia, or generalized anxiety disorder (GAD). In additional embodiments, the method further comprises if the discrimination index is less than or equal to 1, then administering a therapy to the subject in an amount sufficient to increase the discrimination index to greater than 1.

In a fourth implementation, a non-transitory, computer-readable medium is provided. The non-transitory, computer-readable medium has instructions stored therein. The instructions, when executed by a processor, cause performance of a set of operations. The operations comprise receiving a cued fear response value of a subject, and receiving a non-cued fear response value of the subject. The operations further comprise determining a discrimination index. The discrimination index is equal to a ratio of the cued fear response value to the non-cued fear response value. The operations additionally include determining a therapy for the subject based on at least the determined discrimination index.

In some embodiments, the operations further comprise outputting a notification if the determined discrimination index is less than or equal to 1. In further embodiments, the operations further comprise displaying the determined discrimination index. In yet further embodiments, the determined discrimination index is a first discrimination index, and the operations further comprise: receiving a second cued fear response value of the subject; receiving a second non-cued fear response value of the subject; determining a second discrimination index, wherein the second discrimination index is equal to a ratio of the second cued fear response value to the second non-cued fear response value; and adjusting the determined therapy based on at least the second discrimination index. In additional embodiments, the operations further comprise displaying the first discrimination index and the second discrimination index. In some embodiments, displaying the first discrimination index and the second discrimination index comprises plotting the first discrimination index and the second discrimination index over time. In further embodiments, the operations further comprise displaying the determined therapy for the subject. In still further embodiments, the operations further comprise: performing a diagnostic process, wherein the diagnostic process comprises: diagnosing a presence of or susceptibility to a stress-induced psychiatric disorder if the discrimination index is less than 1 or equal to 1; and diagnosing an absence of or resilience to a stress-induced psychiatric disorder if the discrimination index is greater than 1. In some embodiments, the stress-induced psychiatric disorder includes at least one of post-traumatic stress disorder (PTSD), panic disorder, a phobia, or generalized anxiety disorder (GAD).

Other aspects, embodiments, and implementations will become apparent by reading the following detailed description with reference, where appropriate, to the accompanying drawings.

BRIEF DESCRIPTION OF THE FIGURES

FIG. 7 shows a table of oxytocin content in the dorsolateral bed nucleus of the stria terminalis, following an example experimental method. Cued (shock+cue), but not contextual fear conditioning (shock alone), increases OT content in $BNST_{dl}$ microdialysates. In contrast, forced swim stress (FS) or social interactions (SI) do not affect OT release in the $BNST_{dl}$. Data are presented as MEAN±standard error of mean (SEM) of OT content in $BNST_{dl}$ microdialysates expressed as pg per 100 μl microdialysis sample. There was a significant TREATMENT effect on OT content in $BNST_{dl}$ microdialysates in rats exposed to cued fear conditioning (P=0.0297, one-way ANOVA.

BRIEF DESCRIPTION OF THE DRAWINGS

FIG. 8 shows a table of percentages of oxytocin neurons co-expressing cFos in various brain sections from the hypothalaumus, following another example experimental method. Cued (shock+cue), but not contextual fear conditioning (shock alone), increases OT content in BNSTdl microdialysates. In contrast, forced swim stress (FS) or social interactions (SI) do not affect OT release in the BNSTdl. Data are presented as MEAN±standard error of mean (SEM) of OT content in BNSTdl microdialysates expressed as pg per 100 μl microdialysis sample. There was a significant TREATMENT effect on OT content in BNSTdl microdialysates in rats exposed to cued fear conditioning (P=0.0297, one-way ANOVA). Fear conditioning activates OT neurons in the hypothalamus. Percentages of OT neurons co-expressing cFos in brain sections from the paraventricular (PVN), supraoptic (SON), as well as accessory nucleus of the hypothalamus (AN) in response to cued (shock and cue), or contextual (shock alone) fear conditioning are shown as MEAN±standard error of mean (SEM). Data are presented in all hypothalamic sections combined (all AREAS) and in grouped hypothalamic sections based on Bregma level from anterior to posterior (AREA 1, Bregma −0.60 mm to 1.20 mm, AREA 2, Bregma −1.32 mm to −1.72 mm, and AREA 3, Bregma −1.80 to −2.28 mm).

Figure 9:
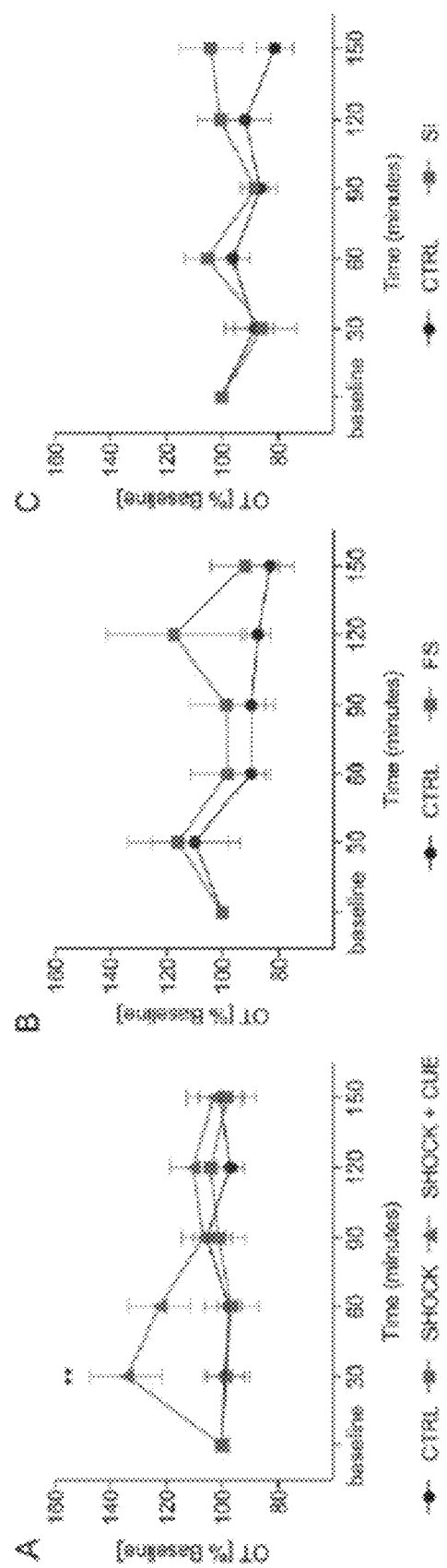

FIG. 9 shows the oxytocin content in microdialysates of the dorsolateral bed nucleus of the stria terminalis following an example fear-potentiated startle paradigm. Cued, but not contextual fear conditioning increases OT content in $BNST_{dl}$ microdialysates (A). Two-way repeated measures ANOVA revealed a significant interaction between TIME and TREATMENT (P=0.0408), and post hoc analysis with Bonferroni's showed a significantly greater percentage change of OT content in $BNST_{dl}$ microdialysates in rats exposed to cued fear conditioning (134.66%±12.95 of baseline content,) at 30 min in comparison to CTRL rats (98.86%±6.56, P<0.01) and rats exposed to contextual fear conditioning (98.29%±8.04, P<0.01). In contrast, forced swim stress (FS, B), or social interactions (SI, C) did not affect OT content in $BNST_{dl}$ microdialysates.

Figure 10:
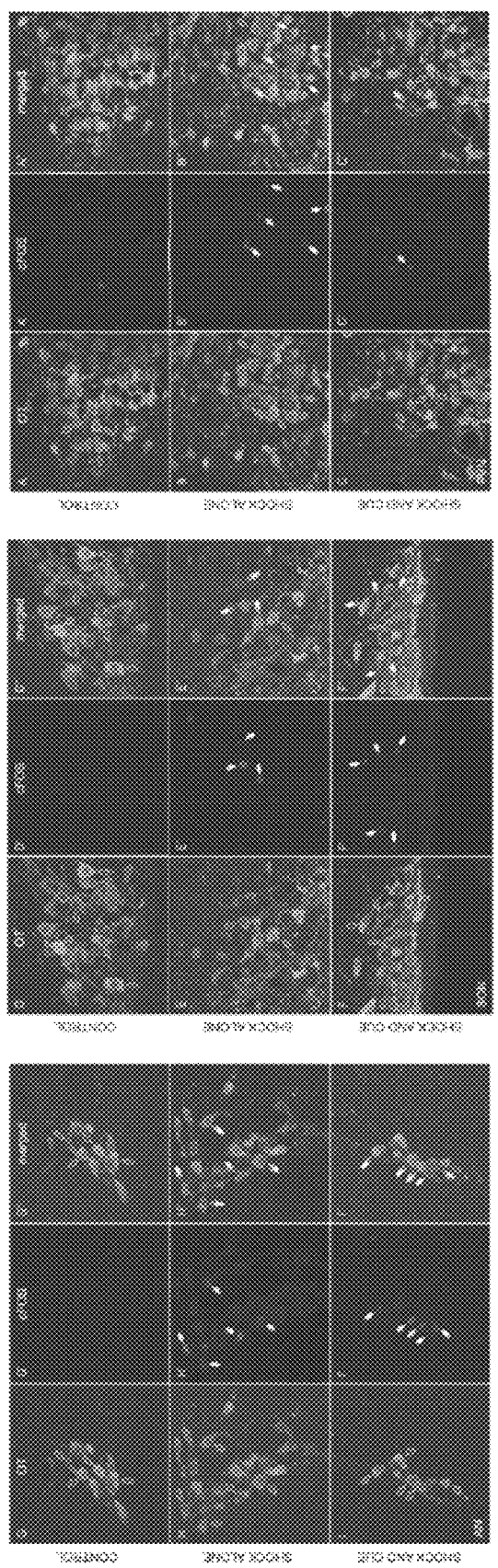

FIG. 10 shows various images of oxytocin neurons in the hypothalamus variably expressing oxytocin and/or cFos, according to an example experimental method. Fear conditioning activates OT neurons in the hypothalamus. While control rats show little co-localization of OT (green, open arrows) and cFos (red, closed arrows) in the PVN (A'-A"), rats exposed to contextual fear conditioning (shock alone, B-B"), but not cued fear conditioning (shock and cue, C-C"), show increase in percentage of neurons co-expressing OT and cFos in the PVN. In the SON, number of neurons co-expressing OT and cFos was significantly increased in response to contextual (E-E") as well as cued fear conditioning (F-F") in comparison to control rats (D-D"). In addition, activation of OT neurons in the SON was greater in rats exposed to contextual vs. cued fear conditioning. Finally, in the AN, percentage of neurons co-expressing cFos and OT was increased in response to both contextual (H-H") as well as cued fear conditioning (I-I"), in comparison to control rats (G-G", magnification 60×).

Figure 11:
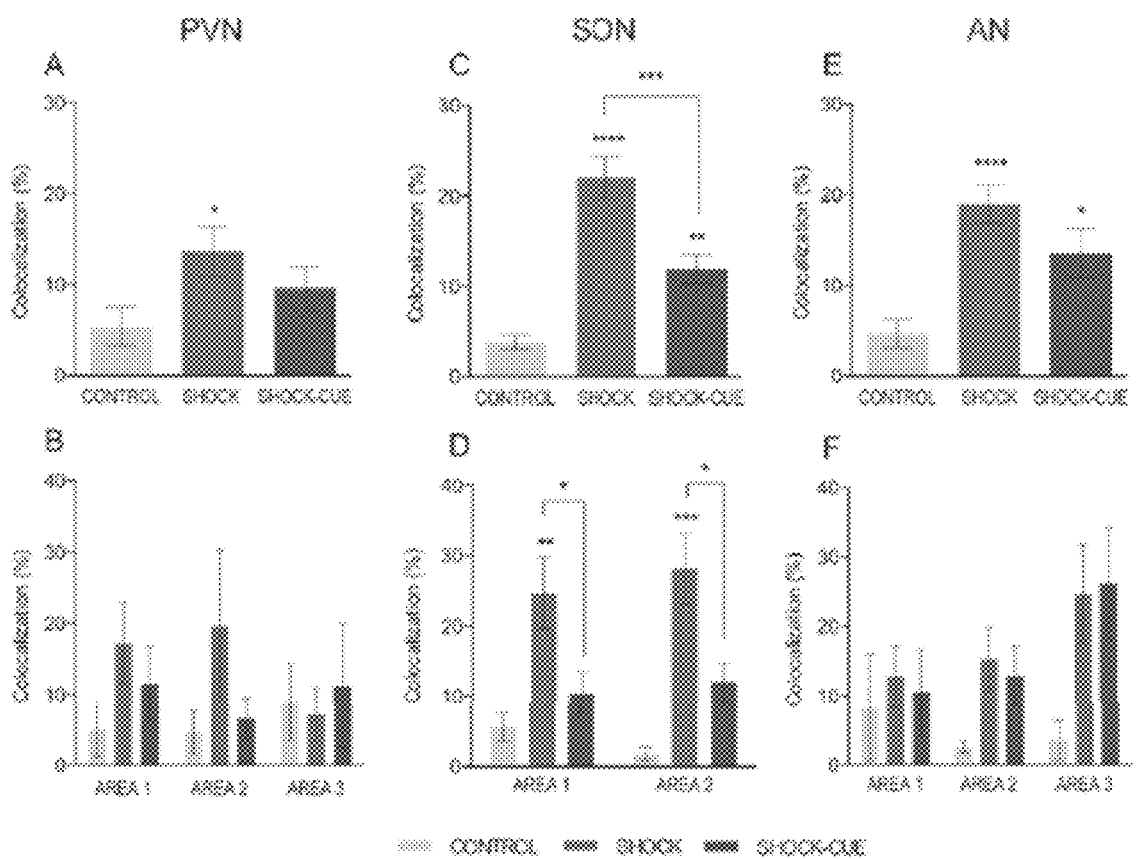

FIG. 11 illustrates the effects of fear conditioning on the percentage of OT neurons co-expressing cFos in the PVN, SON, and AN. (A) In the PVN, there was a significant effect of fear conditioning on OT neurons activation (P=0.0465), with a significantly greater percentage of activated OT neurons in rats exposed to contextual fear conditioning (shock) in comparison to control rats (*P<0.05, B). There was no interaction between condition and AREAS 1-3 observed in the PVN. (C) OT neurons within the SON were significantly activated in response to fear conditioning (P<0.0001, one-way ANOVA), with a greater percentage of OT neurons co-localizing cFos in rats exposed to contextual fear conditioning compared to control rats (**P<0.0001), as well as in rats exposed to cued fear conditioning (shock-cue) compared to controls (P<0.01). Finally, there was a greater activation of OT neurons in response to contextual vs. cued fear conditioning in the SON (*P<0.001). (D) Comparing percentages of activated OT neurons across AREAS 1-2 in the SON, showed a significant effect of condition. In AREA 1, post-hoc rest revealed a significant activation of OT neurons in rats exposed to contextual fear conditioning in comparison to control rats (P<0.01) and in comparison to rats exposed to cued fear conditioning (*P<0.05). Similarly, in AREA 2, a greater percentage of activated OT neurons was observed in rats exposed to contextual fear conditioning compared to controls (***P<0.001) and compared to rats exposed to cued fear conditioning (*P<0.05). (E) Fear conditioning activated OT neurons in the AN (**P<0.0001, one-way ANOVA), with a significantly greater percentage of activated OT neurons in rats exposed to contextual fear conditioning (**P<0.0001), and in rats exposed to cued fear conditioning (*P=0.0168), compared to control rats. (F) There was no significant effect of condition, AREA, or interaction when comparing percentages of OT neurons across AREAS 1-3.

Figure 12:
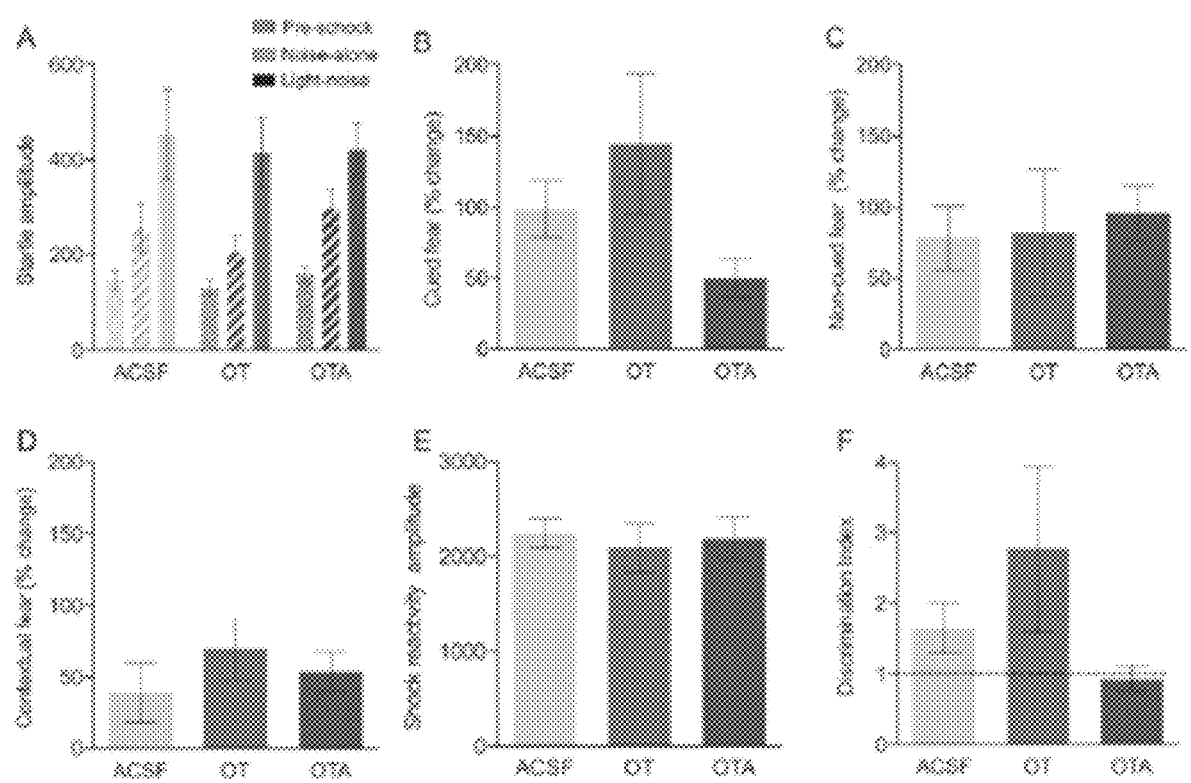

FIG. 12 illustrates the effects of intra-$BNST_{dl}$ administration of ACSF, OT, or OTA on the FPS acquisition. Group data for pre-shock, noise-alone, and light-noise startle amplitude from rats given bilateral intra-$BNST_{dl}$ ACSF (n=23, gray), OT (100 ng, n=14, red), or OTA (200 ng, n=16, blue), 10 min prior to the fear conditioning session. All rats exhibited a significantly potentiated startle response in light-noise trials compared to noise-alone trials (P<0.0001), but this was not affected by the treatment (A). There was a trend toward TREATMENT effect on the percentage change of cued fear in rats given intra-$BNST_{dl}$ ACSF, OT or OTA (P=0.0981 (B). All rats exhibited a significant potentiation of startle amplitude in noise-alone trials in comparison to pre-shock ASR (P<0.0001), but it was not affected by intra-$BNST_{dl}$ injections (A). There was no TREATMENT effect on percentage change on non-cued fear (P=0.8993) (C), contextual fear (P−0.5384 (D), or shock reactivity (P−0.8684) (E). Comparing discrimination indices from all trials in rats injected with ACSF, OT, and OTA did not show any significant effect of TREATMENT (P=0.1492 (F).

Figure 13:
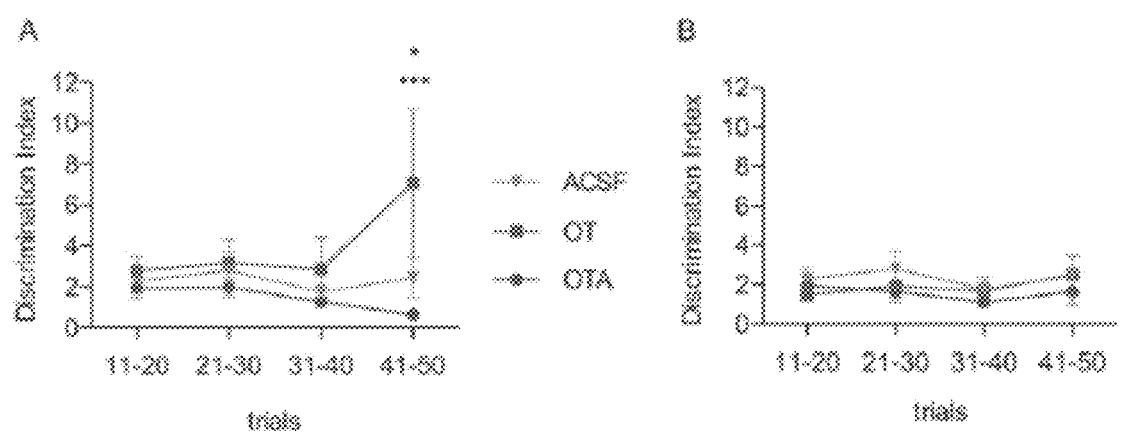

FIG. 13 illustrates the effects of intra-$BNST_{dl}$ administration of ACSF, OT, or OTA on discrimination index (DI)

measured in four time blocks during fear memory recall. Each block consists of 5 noise-alone trials and 5 light-noise trials, which have been used to calculate DI in each block. (A). There was a significant interactions between TIME and TREATMENT (P=0.0406) and Bonferroni's post hoc tests showed a significant difference in the fourth time block between DI of rats injected with ACSF and OT (P=0.0121) as well as rats injected with OT and OTA (P=0.0007, ***P<0.001, *P<0.05). (B). DI calculated over four time blocks during fear memory recall in negative controls (injection sites outside the $BNST_{dl}$ showed no main effect of TREATMENT (P=0.5828), nor an interaction between TIME and TREATMENT (P=0.9634).

DETAILED DESCRIPTION

Example methods, devices, and systems are presently disclosed. It should be understood that the word "example" is used in the present disclosure to mean "serving as an instance or illustration." Any implementation or feature presently disclosed as being an "example" is not necessarily to be construed as preferred or advantageous over other implementations or features. Furthermore, unless otherwise specified and/or unless the particular context clearly dictates otherwise, the terms "a" or "an" mean at least one, and the term "the" means the at least one. Other implementations can be utilized, and other changes can be made, without departing from the scope of the subject matter presented in the present disclosure.

Thus, the example implementations presently disclosed are not meant to be limiting. Components presently disclosed and illustrated in the figures can be arranged, substituted, combined, separated, and designed in a wide variety of different configurations, all of which are contemplated in the present disclosure.

Further, unless context suggests otherwise, the features illustrated in each of the figures can be used in combination with one another. Thus, the figures should be generally viewed as components of one or more overall implementations, with the understanding that not all illustrated features are necessary for each implementation.

In an effort to provide technical context for the present disclosure, the information in this section can broadly describe various components of the implementations presently disclosed. However, such information is provided solely for the benefit of the reader and, as such, does not expressly limit the claimed subject matter. Further, components shown in the figures are shown for illustrative purposes only. As such, the illustrations are not to be construed as limiting. As is understood, components can be added, removed, or rearranged without departing from the scope of this disclosure.

I. OVERVIEW

For particular applications, it could be beneficial to provide a method and system for measuring an individual's ability to discriminate between signaled and un-signaled fear, for instance, fear measured during fear-potentiated startle (FPS) paradigm. In some cases, a medical professional may desire to assess an individual's diagnosis or susceptibility to a stress-induced psychiatric disorder, e.g., post-traumatic stress disorder (PTSD), panic disorder, phobias or generalized anxiety disorder (GAD), in a way that is standardized, quantitative and/or repeatable. Similarly, it may be beneficial to provide a method for evaluating the progression of a stress disorder and/or the efficacy of a therapy in stress disorder patients.

The present disclosure generally relates to a system and method for determining a discrimination index, which may compare a subject's reaction to cued (i.e., signaled) fear and non-cued (i.e., non-signaled) fear. Cued fear response may be measured as a startle potentiation observed during presentation of a cue, which has been previously paired with an aversive or threatening stimulus (e.g., a foot shock). Non-cued fear response may be measured as a startle potentiation between cue presentations, which is observed after a subject is presented with at least one cue. The discrimination index (DI) may be equal to a ratio, for instance, a ratio calculated by dividing a cued fear response value and a non-cued fear response value (or vice versa). In such a case, a DI or greater than 1 would indicate that the subject's reaction is biased toward signaled threats, i.e., the subject has a stronger reaction to stimuli conditioned to be threatening. Conversely, a DI that is less than 1 would indicate that the subject has difficulty discriminating between threatening and non-threatening stimuli, and may react to non-threatening stimuli more strongly due to, e.g., background anxiety and/or a stress-induced psychiatric disorder. A DI equal to 1 indicates that the subject responds to cued and non-cued stimuli equally.

The discrimination index calculation described above could be implemented when comparing cued and non-cued fear responses as part of a FPS paradigm. In one example, a subject is exposed to a first threatening stimulus (i.e., a stimulus previously paired with an aversive stimulus, e.g., a foot shock) and a reflexive physiological reaction (i.e., a startle response) is measured in response to the threatening stimulus. The first stimulus includes a startling stimulus (e.g., a noise) configured to startle the subject and a cueing stimulus (e.g., a visual or auditory stimulus) that has been conditioned to invoke fear in the subject. The startle response to this first stimulus could represent a cued fear response. The same subject may also be exposed to a second non-threatening stimulus, which includes the same startling stimulus without the conditioned cueing stimulus. (i.e., such that the second stimulus evokes a startle, but is not conditioned to be fear-inducing). A second reflective physiological reaction (i.e., startle response) is measured in response to the second stimulus, and may represent a non-cued fear response. The non-cued fear response may be measured as a startle potentiation between cued fear trials, after the subject has been exposed to at least one cueing stimulus.

In some cases, the raw values measured as described above may be used to calculate the discrimination index. However, generally, a cued fear response value and non-cued fear response value are derived from the measured startle responses after, e.g., filtering, processing, and/or additional calculations. In a particular example, the cued fear response value and non-cued fear response value represent a percentage change in the measured startle response between two or more types of trials. For example, in a specific embodiment the cued fear response value is equal to a percent change between the subject's startle response measured during the cued fear trial and a startle response measured during the non-cued fear trial. The "cued fear response value" of the present disclosure could therefore refer to the percent change in startle response due to the addition of the fear-conditioned cueing stimulus in the cued fear trial. Similarly, the "non-cued fear response value" of the present disclosure could be calculated by determining a percentage change between the non-cued fear trial and a previously-measured baseline startle response occurring before fear conditioning. The non-cued fear response value could therefore represent a percentage change in the subject's startle response due to the conditioning step alone (i.e., background anxiety).

A discrimination index can be determined by taking a ratio between the cued and non-cued fear response values (e.g., by dividing the cued fear response value by the non-cued fear response value, or vice versa). Based on the calculated discrimination index, a medical professional may then make a determination relating to a diagnosis, susceptibility, progression, or treatment of a stress-induced psychiatric disorder.

In a particular example, the discrimination index may be used to determine whether a treatment is needed for a patient suffering from a stress-induced psychiatric disorder. If the determined DI is less than or equal to 1, for example, a physician may administer a pharmaceutical agent (e.g., oxytocin) or prescribe an evidence-based psychotherapy to the patient in order to increase the patient's DI to greater than 1. In some cases, the discrimination index may be used to determine an optimal and/or recommended therapy to best improve a patient's prognosis. A particular type, dosage, or schedule of a therapy may be selected based on at least the determined discrimination index. In a particular example, certain DI values or ranges may correspond to recommending an evidence-based psychotherapy (e.g., exposure therapy, cognitive behavioral therapy, talk therapy), while another DI range may correspond to a recommendation of a pharmaceutical treatment (e.g., intranasal oxytocin). In another example, the dosage of the recommended and/or administered therapy could be based on the determined discrimination index. For instance, a lower discrimination index may result in a higher recommended dosage of the therapy, while discrimination indices approaching or equal to 1 may result in a lower recommended dosage. Other uses of the discrimination index for administering treatment are contemplated.

In another application, a discrimination index may be used to evaluate the efficacy of a treatment of a stress-induced psychiatric disorder. Before conducting the FPS paradigm and/or providing the cued and non-cued fear response values, a treatment could be administered to a patient. The efficacy of the treatment could then be determined by calculating the patient's DI, allowing for evaluation of the current therapy and/or tailoring of future therapies. If the determined DI is more than 1 (or progressively increasing to 1 or more), the therapy could be considered effective and/or continued. Conversely, if the determined DI is less than or equal to 1 (or progressively decreasing to 1 or less), the therapy could be considered ineffective and/or adjusted in the future. In some cases, after determining the DI, an additional therapy may be given to the patient. The additional therapy could be the same as the original therapy, an adjusted dose of the same therapy, or an entirely different pharmaceutical agent and/or evidence-based psychotherapy, depending on the determined DI, efficacy, and/or the needs of the patient.

In still further applications, a discrimination index may provide a way of diagnosing, scoring, or evaluating a stress-induced psychiatric disorder like PTSD, GAD, phobias, or panic disorder. For example, if the determined DI is less than or equal to 1, a physician may determine that a patient has a diagnosis or susceptibility to a stress-induced psychiatric disorder. Similarly, a DI of greater than 1 could indicate an absence or resilience to a stress-induced psychiatric disorder. Such a positive diagnosis may be paired with administering a therapy in order to treat the patient's disorder (i.e., in order to progressively increase the DI to greater than 1).

Any of these methods may also be implemented by a computer-readable medium, software, application, or another system having instructions stored therein to determine a discrimination index. Such a computer-readable medium could include a user interface, display, or communication interface to improve and/or facilitate calculation and use of the DI. Some imagined features could include displaying and/or plotting the DI over time, outputting a notification to a user (e.g., a physician, a psychologist, or the subject) if the DI falls outside of a predetermined range, and/or displaying a diagnosis or recommended therapy (i.e., type, dosage, of schedule) to the user on the display. In some examples, the computer-readable medium could be configured to store the information (e.g., information relating to the discrimination index, therapy, diagnosis, and/or efficacy) and/or transmit the information via the communication interface. Such information may be transmitted to an associated device (e.g., a cellphone or computer), an associated user (e.g., a physician, a patient, a psychologist, or a pharmacist), and/or uploaded to a server or cloud computing platform. Other features are also imagined.

Such a system and method may facilitate the diagnosis, monitoring, and treatment of psychiatric disorders like PTSD, GAD, phobias, and/or panic disorders. By providing physicians a uniform method of diagnosis and treatment, a DI may streamline the treatment of patients with stress-induced psychiatric disorders, improving patient outcomes and treatment efficacy. Similarly, a standardized DI may provide a means for psychologists, researchers, and clinicians to harmonize and more easily compare data, allowing for more robust experimental research on mental illness diagnosis, progression, and treatment. Other implementations and advantages are envisioned.

II. EXAMPLE METHODS

Figure 1:
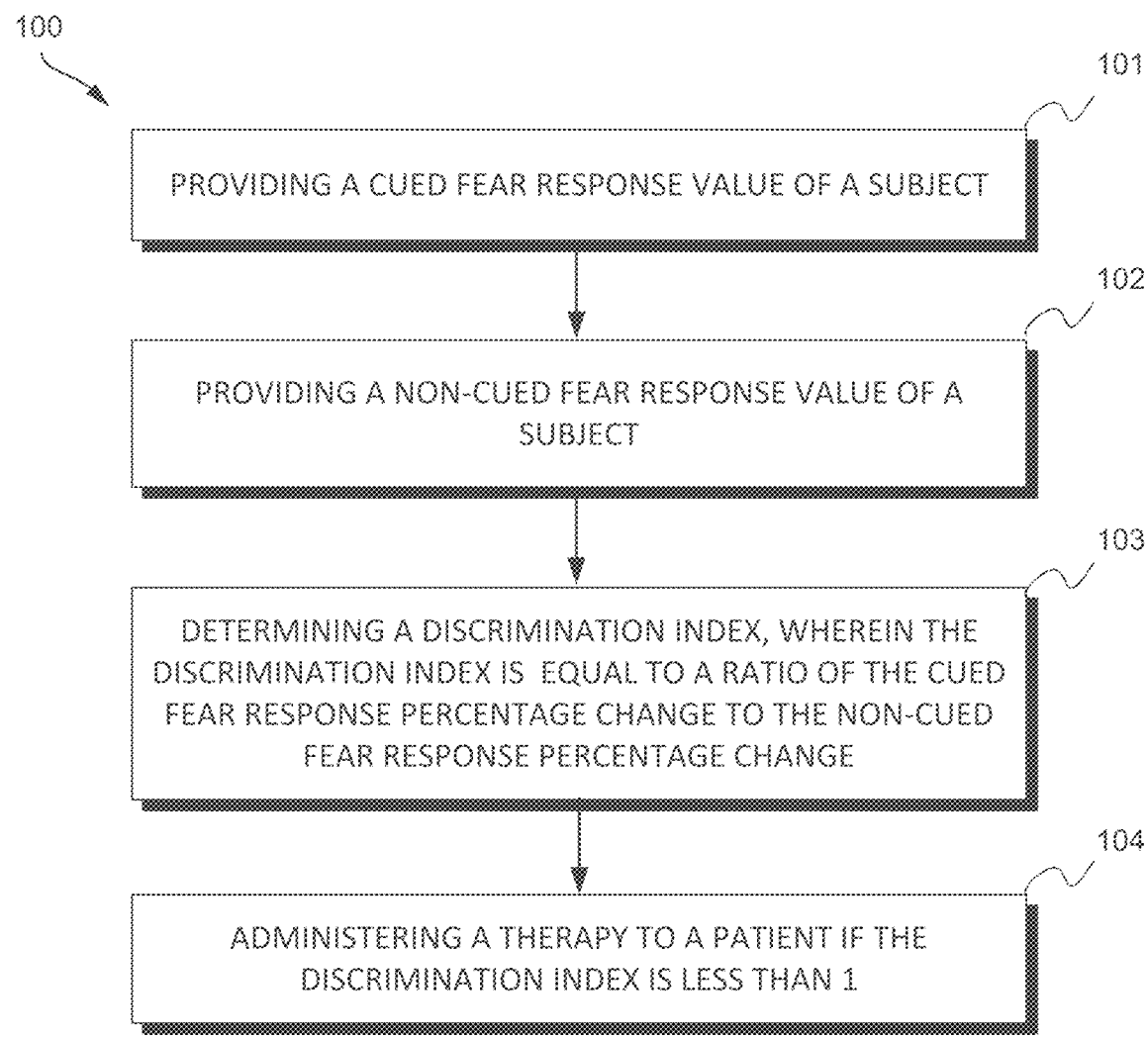
FIG. 1 illustrates a flow chart of a method, according to an example embodiment.

FIG. 1 illustrates a flowchart of a method 100. Block 101 of the method includes providing a cued fear response value of a subject. Block 102 of method 100 includes providing a non-cued fear response value of the subject. Providing a cued fear response value of a subject and providing a non-cued fear response value of the subject could include measuring a cued startle response and a non-cued startle response as part of a FPS paradigm. Such a fear-potentiated startle paradigm, as understood in the art, could include a range of experimental methodologies. For example, various non-limiting examples of FPS procedures are described in (Acheson et al., 2013; Ayers et al., 2011; Fani et al., 2015; Glover et al., 2011; Janeček and Dabrowska, 2018; Missig et al., 2010; Moaddab and Dabrowska, 2017; Walker et al., 2009).

Generally, a FPS paradigm seeks to assess a subject's learned fear response to a cueing stimulus that has been conditioned to be fear-inducing. The cueing stimulus could include any sensory stimuli capable of being classically conditioned to be associated with a negative consequence. In one example, the cueing stimulus could be a visual stimulus, for instance, at least one of a light, a visual pattern, a shape, a face, a screen, or an image. However, other cueing stimuli may be possible, for instance, auditory stimuli (e.g., a beep, a burst of noise, a song, or a tune). Other sensory stimuli are contemplated. This conditioned fear response to the cueing stimulus can then be compared to un-cued fear (i.e., a subject's response to a non-cueing stimulus that has not be conditioned to induce fear) to indicate a subject's mental state or predisposition to a psychiatric disorder.

During FPS, each of the cueing and non-cueing stimuli is paired with a startling stimulus that is configured to elicit a startle response from the subject. The startling stimulus could be, for instance, a burst of white noise (i.e., a white noise burst, WNB) or another auditory stimulus. Additionally or alternatively, the startling stimulus could be a visual stimulus, for instance, a burst of light or an image. However, other startling stimuli may be possible according to the present disclosure. In some examples, method 100 includes measuring a baseline startle response of the subject to the startling stimulus. The baseline startle response could represent the subject's physiological response to the startling stimulus prior to fear conditioning (i.e., before the subject has been conditioned to associate the cueing stimulus with a fear-inducing negative consequence).

After determining a baseline fear response, the subject may undergo conditioning such that they begin to associate the cueing stimulus (i.e., a conditioned stimulus) with a negative consequence (an unconditioned negative stimulus, e.g., a shock). In some examples, method 100 includes a conditioning step configured to condition the cueing stimulus to be fear-inducing. Conditioning could include presenting the subject with a cueing stimulus paired to (i.e., presented concurrently with) a negative consequence for a number of trials, such that the subject associates the cueing stimulus with the negative consequence. The negative consequence may be configured to elicit an increased fear response from a subject. For example, the negative consequence could include an electric shock, a vibration, an auditory stimulus, a visual stimulus, an air puff, or some other sensory stimulus configured to elicit fear from the subject.

To provide the cued and non-cued fear responses, a subject's startle response may be measured following exposure to the cueing and non-cueing stimulus, respectively. Such measurements may generally occur after the conditioning steps described above, however, any number of orders of the steps may fall within the present disclosure. In some examples, method 100 includes presenting the subject with one or more cueing stimuli and/or one or more non-cueing stimuli, and measuring a cued and non-cued fear response, respectively. Presenting the cueing stimulus may include presenting the startling stimulus paired with (i.e., presented concurrently with) the cueing stimulus. Presenting the non-cueing stimulus could include presenting the startling stimulus without the cueing stimulus.

In some examples, providing the cued fear response value and non-cued fear response value could include measuring a startle response of a patient following exposure to the cueing and non-cueing stimuli, respectively. Generally, the cued startle response may be measured as a startle potentiation observed during or in reaction to presentation of the cueing stimulus. Non-cued fear response may be measured as a startle potentiation measured between cue presentations in the absence of the cueing stimulus. Such a non-cued startle potentiation may be observed after the subject is presented with the cueing stimulus at least once.

Measuring the startle response of the subject could include measuring the amplitude of an eyeblink of the subject. In some cases, measuring eyeblink amplitude could include measuring eyelid movement by way of a potentiometric, photoelectric, vertical electrooculographic (vEOG), or magnetic search coil method. However, in other examples eyeblink amplitude may be measured as a voltage response using an electromyograph (EMG), i.e., through an electrode placed proximate to or in contact with a muscle of a subject. In some cases, the electrode could be a needle inserted into the subject such that it contacts the orbicularis oculi muscle, however, in other cases the electrode is a surface electrode positioned proximate to the eye of the subject (e.g., on the skin above the orbicularis oculi muscle). In such examples, providing the cued and/or non-cued fear response value could include measuring a peak voltage (i.e., a startle amplitude and/or eyeblink amplitude) during a discrete period of time following exposure to the cueing and/or non-cueing stimulus. In a particular example, the cued startle response and the non-cued startle response are equal to the measured peak voltage within 200 ms of the presentation of the cueing stimulus and the non-cueing stimulus to the subject, respectively. However, other periods of time may be used, e.g., 50 ms, 100 ms, 500 ms, 1 s, etc. In some cases, a plurality of startle responses (i.e., one or more measurements from one or more trials) may be averaged in order to provide the cued fear response value and/or non-cued fear response value. Further processing could include amplification, rectification, noise reduction, and/or filtering with a band-pass filter or filters. Additional signal processing steps may be anticipated.

Further calculation steps may be used to derive the cued fear response value and the non-cued fear response value from the measured startle responses. For example, in some cases the cued fear response value is equal to a percentage change between the cued startle amplitude and the non-cued startle amplitude, such that it represents a difference in startle amplitude related to the presence of the cueing stimulus. Similarly, the non-cued fear response value may be equal to a percentage change between the non-cued startle amplitude and a baseline startle amplitude (e.g., a baseline startle amplitude in response to the startling stimulus, measured prior to the conditioning step), such that it represents a difference in startle amplitude related to fear conditioning. In other examples the cued and non-cued fear response values could be equal to some other relationship between the cued startle amplitude, the non-cued startle amplitude, and/or the baseline startle amplitude (e.g., a difference in magnitude, an absolute difference, or some other relationship). Other methods of providing the cued fear response value and non-cued fear response value are contemplated.

Block 103 of method 100 includes determining a discrimination index. The discrimination index is equal to a ratio of the cued fear response value to the non-cued fear response value. As used herein "a ratio" refers to the relationship between two amounts showing the number of times one value contains or is contained within the other (e.g., a/b; b/a; cued fear/non-cued fear, etc.). A ratio of the cued fear response value to the non-cued fear response value could be equal to the cued fear response value divided by the non-cued fear response value. In such an example, the determined discrimination index may typically range from about 0.75 to about 3, or more generally from about 0.5 to about 4. A discrimination index greater than 1 indicates the subject has an increased cued fear response relative to the non-cued fear response. A discrimination index of less than 1 or equal to 1 indicates that the subject has an equal or greater response to a non-cued stimulus, and may be associated with a greater risk for a stress-induced psychiatric disorder. Alternatively, the ratio could be a ratio equal to the non-cued fear response value divided by the cued fear response value. In this example, a discrimination index greater than 1 could indicate that the subject is unable to discriminate between cued and non-cued fear (i.e., has an equal or greater non-cued fear response compared to the cued fear response).

In some examples, method 100 could include determining whether the discrimination index is greater than or equal to a predetermined threshold value. In some examples, and as described above, the threshold value could be equal to 1. A discrimination index of greater than 1 could indicate a generally good prognosis (i.e., a diagnosis of an absence of or resilience to a stress-induced psychiatric disorder), while a discrimination index of less than 1 or equal to 1 could indicate a poor prognosis (i.e., a diagnosis of a presence of or susceptibility to a stress-induced psychiatric disorder). However, other threshold values are contemplated (e.g., 0.5, 0.6, 0.7, 0.75, 0.8, 0.9, 1.1, 1.2, 1.25, 1.5, 2, etc.). In some cases, a plurality of threshold values may be used to discern a plurality of diagnoses, stages, risk factors, or other aspects of a stress-induced psychiatric disorder.

Block 104 of method 100 includes administering a therapy to the subject. The administered therapy could include an evidence-based psychotherapy, for instance, talk therapy, cognitive behavioral therapy (CBT), prolonged exposure therapy or another form of psychotherapy. In some cases, the therapy could include a pharmaceutical agent. The pharmaceutical agent could include oxytocin (or an oxytocin analogue and/or biosimilar). Administering the therapy could include administering intranasal oxytocin as, e.g., a nasal spray, a drop(s) of liquid medication, an inhaled particle or aerosol. However, in other examples, administering the therapy could include orally, intravenously, intramuscularly, rectally, or bucally administering oxytocin. Alternative pharmaceutical agents and methods of administration are also contemplated.

In some examples, the therapy may be administered if the discrimination index is less than 1 or equal to 1. However, as described previously, any number of threshold values may be used in order to e.g., determine a patient's prognosis and/or inform their treatment. In alternative embodiments, the method could include administering a therapy to the subject if the discrimination index is less than, greater than, or equal to some other predetermined threshold value (e.g., 0.5, 0.6, 0.7 0.8, 0.9, 1.1, 1.25, 1.5, 2, or some other value).

In some cases, the type, schedule, and/or dosage of the therapy may be selected such that administration of the therapy causes a measurable change in the determined discrimination index or a future determined discrimination index. For example, the therapy may be sufficient to increase the discrimination index to greater than 1. However, in other cases, the therapy may be sufficient to increase the discrimination index by a different amount, decrease the discrimination index by a given amount, maintain a predetermined discrimination index, or have some other effect on the DI. In this context, the term "sufficient" may be used to indicate that a dosage, type, schedule, frequency, bioavailability, exposure, efficacy, or some other aspect of a therapy is adequate to, e.g., progressively improve the discrimination index to a desired value. In some examples, the type, schedule, and/or dosage of the therapy could depend on the discrimination index, and method 100 could include determining a therapy based on at least the determined discrimination index. Additional factors may also play a role in determining the type, schedule, or dosage of the therapy. For instance, the therapy may additionally be based on an age, a weight, a disease state, or a medical history of the subject.

Figure 2:
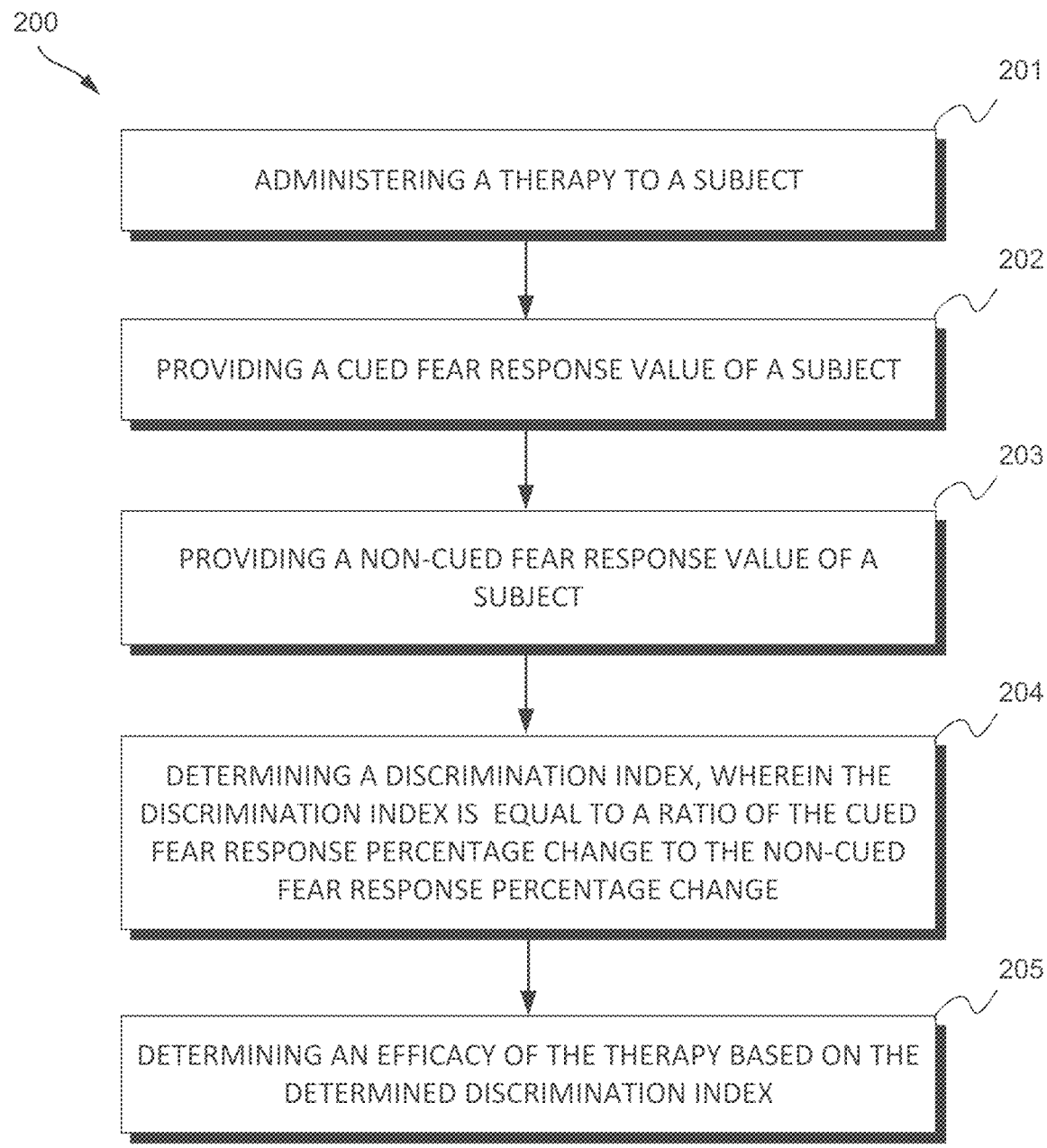
FIG. 2 illustrates a flow chart of a method, according to another example embodiment.

In a second example, the present disclosure could include a method of monitoring progression and/or treatment of a stress-related psychiatric disorder. FIG. 2 illustrates a flowchart of such a method 200. Block 201 includes administering a therapy to a subject suffering from a stress-induced psychiatric disorder. In some cases, the stress-induced psychiatric disorder includes at least one or PTSD, panic disorder, a phobia, or GAD; however, other stress-related psychiatric disorders are anticipated. Administering a therapy could include administering a pharmaceutical agent, as described above in relation to block 104 of method 100. In some examples, administering a therapy could include administering oxytocin, or, more specifically, intranasal oxytocin. Additionally or alternatively, the administered therapy could include an evidence-based psychotherapy, for instance, talk therapy, cognitive behavioral therapy (CBT), or another form of psychotherapy.

Block 202 of method 200 includes providing a non-cued fear response value of the subject. Block 203 of method 200 includes providing a non-cued fear response value of the subject. Block 204 of method 200 includes determining a discrimination index. The discrimination index may be equal to a ratio of the cued fear response value to the non-cued fear response value. As described previously in relation to block 103 of method 100, the ratio may be equal to the cued fear response value divided by the non-cued fear response value. However, determining a discrimination index could include dividing the non-cued fear response value by the cued fear response value, calculating some other relationship between the cued and non-cued fear response values, and/or determining some other relationship between the cued startle response and the non-cued startle response. Blocks 202, 203, and 204 of method 200 may be performed similarly to blocks 101, 102, and 103 of method 100, respectively. Any alternatives and variations in the respective steps of method 100 may also be applied to the steps of method 200, and vice versa.

Block 205 of method 200 includes determining an efficacy of the therapy based on at least the determined discrimination index. The efficacy could be indicative of the effectiveness of the therapy (e.g., the effectiveness pharmaceutical agent or evidence-based psychotherapy) in reducing the symptoms, slowing the progression, or treating a stress-induced psychiatric disorder. In some examples, determining an efficacy of the therapy based on at least the determined discrimination index could include determining whether the discrimination index is less than or equal to a predetermined threshold value. In a particular example, determining the efficacy of the therapy could include determining that the therapy is effective if the discrimination index is greater than 1. Similarly, determining the efficacy of the therapy could include determining that the therapy is not effective if the discrimination index is equal to or less than 1. However, in other examples, the therapy may be considered effective or not effective if the discrimination index is less than, greater than, or equal to some other predetermined threshold value (e.g., 0.5, 0.6, 0.7 0.8, 0.9, 1.1, 1.25, 1.5, 2, etc.).

In some cases, a therapy may be deemed effective if it is progressively improving symptoms associated with the stress-induced psychiatric disorder, e.g., background anxiety, a discrimination index, or some other symptom. In such a case, determining the efficacy of the therapy could include determining whether the discrimination index is progressively increasing or decreasing to a desired value or at a desired rate. This could include determining a difference between the determined discrimination index and a previously-determined discrimination index, or a rate of change between a plurality of determined discrimination indices. In a particular case, determining the efficacy of the therapy could include determining that the therapy is effective if the discrimination index is progressively increasing to 1 or more. Likewise, determining the efficacy of the therapy could include determining that the therapy is not effective if the discrimination index is progressively decreasing to 1 or less.

In yet further examples, a therapy may be considered effective if a discrimination index is maintained at a predetermined value (e.g., a value corresponding to a healthy prognosis or a value previously deemed effective). Determining an efficacy of a therapy may then include determining that the discrimination index is substantially unchanged (i.e., approximately equal to a previously determined discrimination index). Additionally or alternatively, the efficacy of the therapy may also be based on additional criteria, for instance, additional physiological data, the medical history of the patient, the presence of symptoms, and/or the presence of side effects related to the therapy. Other threshold values, rates of increase or decrease, and/or criterion for determining an efficacy may also be anticipated by one of skill in the art.

Method 200 could further include administering an additional therapy to the subject. The additional therapy could include the same pharmaceutical agent or evidence-based psychotherapy as the therapy administered in block 201 of the method. In examples where the discrimination index is greater than 1 and/or the therapy is determined to be effective, administering the therapy could include administering a same amount, type, dosage, and/or schedule of the therapy. In other examples (e.g., in examples where the discrimination index is less than or equal to 1 and/or the therapy is determined to be ineffective), method 200 could include administering an adjusted amount of the therapy to the subject. The adjusted amount of the therapy may be sufficient to increase the discrimination index to greater than 1. However, in other examples, the adjusted amount of the therapy may be sufficient to progressively increase or decrease the discrimination index to a different predetermined value or at a predetermined rate, maintain the discrimination index at some value, or affect the discrimination index by some other amount. Additionally or alternatively, the additional therapy could include a different therapy (i.e., a different pharmaceutical agent or evidence-based psychotherapy than the therapy administered in block 201 of the method).

A type, schedule, and/or dosage of the additional therapy may be determined based on at least the efficacy and/or discrimination index of the therapy. In such an example, method 200 could further include determining an additional therapy based on at least the determined discrimination index and/or efficacy. A type, schedule, and/or dosage of the therapy may be selected such that the therapy is sufficient to improve the subject's discrimination index (e.g., sufficient to increase the discrimination index to greater than 1, etc.). In some examples, method 200 includes outputting the determined therapy on a display. Additionally or alternatively, the therapy may be transmitted to an associated device, and/or user via, e.g., a wired or wireless connection to an external device.

Figure 3:
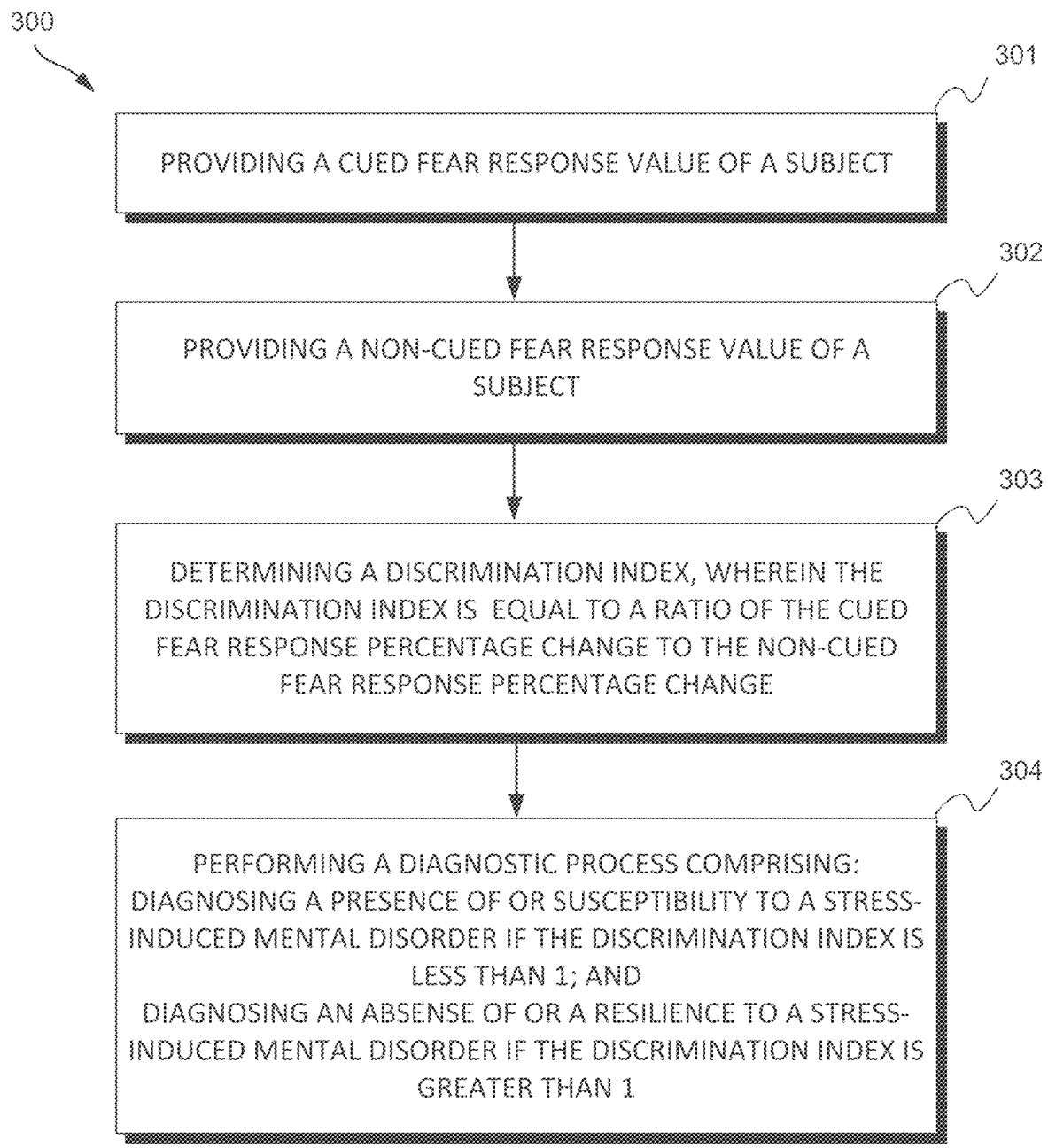
FIG. 3 illustrates a flow chart of a method, according to a further example embodiment.

In other examples, the present disclosure could include determining a discrimination index in order to perform a diagnostic process. FIG. 3 shows a flowchart of such an example method 300. Block 301 of method 300 includes providing a non-cued fear response value of the subject. Block 302 of method 300 includes providing a non-cued fear response value of the subject. Block 303 of method 300 includes determining a discrimination index. The discrimination index may be equal to a ratio of the cued fear response value to the non-cued fear response value. Blocks 301, 302, and 303 may be performed similarly to blocks 101, 102, and 103 of method 100 or blocks 202, 203, and 204 of method 300, respectively. Any alternatives and variations in the respective steps of method 100 may also be applied to the steps of method 200, and vice versa.

Block 304 of method 300 includes performing a diagnostic process. Performing the diagnostic process could include diagnosing a presence or absence of a stress-induced psychiatric disorder if the discrimination index is less than or greater than a predetermined threshold value. In a specific example, performing the diagnostic process includes diagnosing a presence of or susceptibility to a stress-induced psychiatric disorder if the discrimination index is less than 1 or equal to 1. In some examples, the diagnostic process further includes diagnosing an absence of or resilience to a stress-induced psychiatric disorder if the discrimination index is greater than 1. However, in other examples, a presence or susceptibility (or, conversely, an absence or resilience) may be diagnosed if the discrimination index is less than, greater than, or equal to some other predetermined threshold value.

In some cases, the stress-induced psychiatric disorder includes at least one of PTSD, panic disorder, a phobia, or GAD. However, other psychiatric disorders may also be diagnosed. In another example, the diagnostic process could be performed to determine a risk factor, progression, severity, stage, or type of a stress-induced psychiatric disorder. Method 300 could include determining a risk factor, progression, severity, stage, or type of a stress-induced psychiatric disorder based on at least the determined discrimination index. Other diagnostic processed may be envisioned by one of ordinary skill in the art.

Additional steps may also be performed responsive to and/or dependent on the diagnostic process. For example, in some examples method 300 includes outputting the diagnosed presence, absence, susceptibility or resilience on a display and/or outputting a notification to a user. In some cases, the diagnosis may be transmitted to an associated device, and/or user via, e.g., a wired or wireless connection to an external device. Method 300 may further include administering a therapy to the subject if the discrimination index is less than or equal to 1. In particular, if the discrimination index is less than or equal to 1, a therapy may be administered in an amount sufficient to increase the discrimination index to greater than 1.

The example methods 100, 200 and 300 illustrated in FIGS. 1, 2, and 3 are meant as illustrative, non-limiting examples. Blocks and steps described herein may be carried out sequentially or in parallel. Furthermore, the various block and steps could be carried out in a different order than described herein and some blocks and steps could be omitted, skipped, and/or repeated. Additional or alternative elements of the methods and additional or alternative components of the systems are contemplated.

III. EXAMPLE SYSTEM

Figure 4:
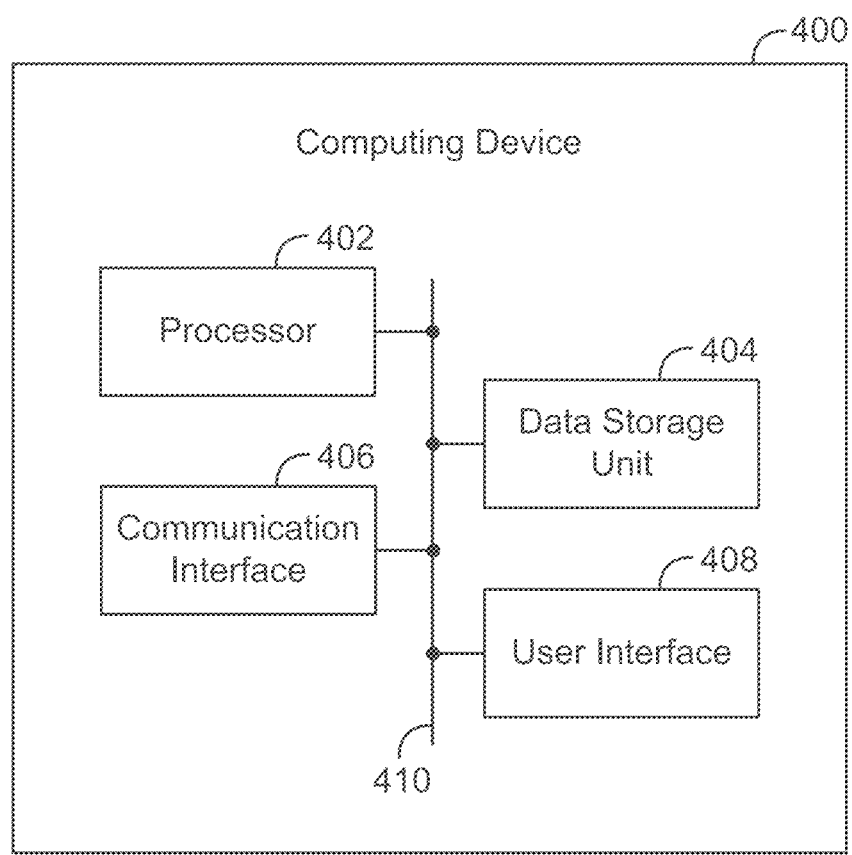
FIG. 4 illustrates a block diagram of an example system.

FIG. 4 is a simplified block diagram of an example computing device 400. The computing device can be configured to perform and/or can perform one or more acts and/or functions, such as those shows in FIGS. 1, 2, and 3 and described herein. The computing device 400 can include various components, such as a processor 402, a data storage unit 404, a communication interface 406, and/or a user interface 408. Each of these components can be connected to each other via a connection mechanism 410.

In this disclosure, the term "connection mechanism" means a mechanism that facilitates communication between two or more components, devices, systems, or other entities. A connection mechanism can be a relatively simple mechanism, such as a cable or system bus, or a relatively complex mechanism, such as a packet-based communication network (e.g., the Internet). In some instances, a connection mechanism can include a non-tangible medium (e.g., in the case where the connection is wireless).

The processor 402 can include a general-purpose processor (e.g., a microprocessor) and/or a special-purpose processor (e.g., a digital signal processor (DSP)). The processor 402 can execute program instructions contained in the data storage unit 404 as discussed below.

The data storage unit 404 can include one or more volatile, non-volatile, removable, and/or non-removable storage components, such as magnetic, optical, and/or flash storage, and/or can be integrated in whole or in part with the processor 402. Further, the data storage unit 404 can take the form of a non-transitory computer-readable storage medium, having stored thereon program instructions (e.g., compiled or non-compiled program logic and/or machine code) that, upon execution by the processor 402, cause the computing device 400 to perform one or more acts and/or functions, such as those described in this disclosure.

The operations performed by the processor 402 could include any of the steps of methods 100, 200, and 300 and described herein. In a particular example, the operations could include receiving a cued fear response value of a subject and receiving a non-cued fear response value of the subject. Receiving the cued and non-cued fear response values could include receiving them via the communication interface 406, e.g., via the Internet or via a wired or wireless connection to an external device. In some instances, receiving the cued and the non-cued fear response value could include inputting the cued fear response value and the non-cued fear response value on the user interface 408 of the computing device 400. In some cases, the operations may further include saving the cued fear response value and the non-cued fear response value on the data storage unit 404.

The operations further include determining a discrimination index. The determined discrimination index could be equal to a ratio of the cued fear response value to the non-cued fear response value, as described above in relation to methods 100, 200, and 300. The program instructions could additionally include saving the determined discrimination index on the data storage unit 404 and/or transmitting the determined discrimination index to an external entity (e.g., an associated computer, a mobile device, or a cloud network server) via the communication interface 406.

The operations additionally include determining a therapy for the subject based on at least the determined discrimination index. As described previously in this disclosure, a type, schedule, and/or dosage of the therapy may be selected such that the therapy is sufficient to increase the subject's discrimination index to greater than 1. The therapy could be, for instance, a pharmaceutical agent (e.g., oxytocin) or an evidence-based psychotherapy (e.g., talk therapy, cognitive behavioral therapy). However, other therapies are contemplated. The program instructions could additionally include saving the therapy on the data storage unit 404 and/or transmitting the therapy to an external entity (e.g., an associated computer, a mobile device, or a cloud network server) via the communication interface 406.

In some examples, the operations further include performing a diagnostic process, such as the diagnostic process described in step 204 of method 200. Such a diagnostic process could include diagnosing a presence of or susceptibility to a stress-induced psychiatric disorder if the discrimination index is less than 1 or equal to 1. The diagnostic process could further include diagnosing the absence of or resilience to a stress-induced psychiatric disorder if the discrimination index is greater than 1. In some cases, the operations could include responding to the presence or absence of a stress-induced psychiatric disorder by, e.g., displaying the diagnosis or outputting a notification on a display device of the computing device 400. The program instructions could additionally include saving the diagnosis on the data storage unit 404 and/or transmitting the determined diagnosis to an external entity (e.g., an associated computer, a mobile device, or a cloud network server) via the communication interface 406.

In some examples, one or more discrimination indices may be calculated from a plurality of trials to e.g., observe DI trends over time, monitor the progression or treatment of a stress-induced psychiatric disorder, or for some other benefit. In such examples, the determined discrimination index could be a first discrimination index, and the operations could further include receiving a second cued fear response value of the subject, receiving a second non-cued fear response value of the subject, and determining a second discrimination index. The second discrimination index may similarly be equal to a ratio of the second cued fear response value to the second non-cued fear response value. The operations could further include adjusting the determined therapy based on the second discrimination in index in order to, e.g., tailor the therapy to the updated needs of the patient. The second discrimination index may similarly be saved to a data storage unit 404 of the computing device 400 and/or transmitted to an external entity via the communication interface 406.

These program instructions may define and/or be part of a discrete software application. In some instances, the computing device 400 can execute program instructions in response to receiving an input, such as from the communication interface 406 and/or the user interface 408. The data storage unit 404 can also store other types of data, such as data relating to a determined discrimination index, efficacy, administered therapy or therapies, patient information, or other types of data described in this disclosure.

The communication interface 406 can allow the computing device 400 to connect with and/or communicate with another other entity according to one or more protocols. In one example, the communication interface 406 can be a wired interface, such as an Ethernet interface or a high-definition serial-digital-interface (HD-SDI). In another example, the communication interface 406 can be a wireless interface, such as a cellular or WI-FI interface. In this disclosure, a connection can be a direct connection or an indirect connection, the latter being a connection that passes through and/or traverses one or more entities, such as a router, switcher, or other network device. Likewise, in this disclosure, a transmission can be a direct transmission or an indirect transmission.

The user interface 408 can include hardware and/or software components that facilitate interaction between the computing device 400 and a user of the computing device 400, if applicable. As such, the user interface 408 can include input components such as a keyboard, a keypad, a mouse, a touch-sensitive panel, a microphone, and/or a camera, and/or output components such as a display device (which, for example, can be combined with a touch-sensitive panel), a sound speaker, and/or a haptic feedback system.

A display device can be used for outputting information, for instance, information relating to the diagnosis, progression, treatment, or severity of a stress-induced psychiatric disorder. In a particular example, the operations could include displaying the first discrimination index and/or the second discrimination index on the display device. In some cases, displaying the first discrimination index and/or the second discrimination index could include plotting the first discrimination index and the second discrimination index over time as, e.g., a graphical display, to show temporal trends in the DI. Additionally or alternatively, the operations could include displaying a determined therapy for a subject on, e.g., the display device. The operations could further include outputting a notification if the determined discrimination is greater than, lower than, equal to, or within a threshold value or range of values (e.g., less than 1 or equal to 1, etc.)

The computing device 400 can take various forms, such as a workstation terminal, a desktop computer, a laptop, a tablet, a mobile phone, a set-top box, and/or a television.

IV. EXAMPLE 1

Oxytocin Receptors in the Dorsolateral Bed Nucleus of the Stria Terminalis (BNST) Enable Discrimination Between Signaled and Un-Signaled Threats Hypothalamic oxytocin (OT) neurons project to the dorsolateral bed nucleus of the stria terminalis ($BNST_{dl}$), a forebrain region critically involved in modulating fear and anxiety. Recently it was shown that blocking OT receptors (OTR) in the $BNST_{dl}$ reduces acquisition of cued fear measured in a fear-potentiated startle (FPS) paradigm (Moaddab and Dabrowska, 2017). Here, an investigation is conducted to determine whether fear conditioning activates hypothalamic OT neurons and modulates OT release in the $BNST_{dl}$. Using in vivo microdialysis in freely moving male Sprague-Dawley rats, it is shown that in contrast to acute stress, exposure to cued fear conditioning increases OT content in $BNST_{dl}$ microdialysates. Next, a double immunofluorescence approach is combined with confocal microscopy to determine the percentage of OT neurons co-expressing cFos in the paraventricular (PVN), supraoptic (SON), and accessory (AN) nuclei of the hypothalamus in response to fear conditioning. It is shown that rats exposed to fear conditioning show moderate activation of OT neurons in the PVN and robust activation in the SON and AN. Finally, to determine the role of OTR in fear memory formation, a selective OTR antagonist or OT was infused into the $BNST_{dl}$ of rats before fear conditioning and their ability to discriminate between cued (signaled) and non-cued (un-signaled) fear was measured using FPS. It is shown that application of OT into the $BNST_{dl}$ significantly increases discrimination between cued and non-cued fear by biasing rats' responses toward signaled threats, whereas blocking OTR disables this discrimination. Results show that OTR neurotransmission in the $BNST_{dl}$ plays a pivotal role in the ability to discriminate between threat and safety.

2. Material and Methods
2.1 Animals

Male Sprague-Dawley rats (Envigo, Chicago, Ill.; 240-300 g at the time of surgery) were housed in groups of three on a 12 h light/dark cycle (light 7 a.m. to 7 p.m.) with free access to water and food. Rats were habituated to this environment for one week before the experiments began. Protocols for animal experiments in this study were performed in accordance with the guidelines of the National Institute of Health and approved by the Animal Care and Use Committee at Rosalind Franklin University of Medicine and Science.

2.2 The Effect of Fear Conditioning, Acute Stress, or Social Interaction on OT Content in $BNST_{dl}$ Microdialysates A total of 72 rats were used in all microdialysis experiments. There were 41 rats used in the forced swim stress and social interaction experiments, but 9 rats were excluded from the analysis due to probe misplacement or inability to unequivocally confirm placement of the probe. Thus, 32 rats were included in the analysis. A total of 31 rats were used in the fear conditioning experiment. However, 6 rats were eliminated due to missing microdialysate samples (e.g. microdialysate containing less than 50 µl) and 2 rats were eliminated due to misplacement of the microdialysis probe. Therefore, a total of 23 rats were included in the analysis.

2.2.1 Microdialysis Probe Implantation

Microdialysis experiments were performed according to previously published protocol (Martinon and Dabrowska, 2018). The two ends of the microdialysis probe were first attached with PE-20 polyethylene tube, followed by flushing and filling of the probe with sterile double distilled water. Standard stereotaxic procedures were used for unilateral implantation of the microdialysis probe. Rats were implanted with probes containing a U-shaped dialysis membrane (molecular cut-off 18 kDa, Hemophan, Gambro Dialysatoren, Hechingen, Germany; for details, see (Neumann et al., 1993) into left $BNST_{dl}$ (coordinates from Bregma: AP+0.1 mm, ML+3.4 mm, DV−7.25 mm, 15° coronal angle). Rats were given an analgesic (5 mg/kg ketoprofen, subcutaneous) prior to the surgery. The surgery was performed with a stereotaxic frame (David Kopf Instruments, USA) using isoflurane anesthesia (E-Z Systems Corporation, Palmer, Pa.). Small stainless steel screws were inserted into the frontal and parietal bones to secure the probe to the skull using acrylic cement. After the surgery was completed, the outlets of the probe were secured with tape to prevent any damage to the probe until the day of the experiment. Ketoprofen was given again the morning after surgery. Rats were caged individually for 2 days prior to starting the microdialysis experiment. This has been shown to be an optimal timeline as chronic implantation of the microdialysis probe increases the risk of gliosis three days after implantation, which significantly reduces absolute and relative recovery of the microdialysis membrane (Hascup et al., 2009).

2.2.2 In Vivo Microdialysis in Freely Moving Rats

Rats were placed individually in Plexiglas cages (43 cm×21 cm×31 cm) for 30 minutes before connecting the probe to the microinjection pump. Rats were gently restrained and the microdialysis probe was connected to a 3-ml syringe mounted on a microdialysis pump (PHD Ultra Pump, Harvard Apparatus) using a 2-channel spiral tubing (CT-20, Eicom, San Diego, Calif., internal volume 4 µl) with connecting Joint Teflon (JT-10, Eicom, San Diego, Calif., 4 µl) and a 2-way swivel (Eicom, San Diego, Calif.). Hence, the total internal volume of inlet and outlet tubing was 16 µl so that any effects of behavioral manipulation could be already observed in the first sample collected post-treatment. This microdialysis study was performed in awake, freely moving rats provided with food and water for the duration of the experiment, except during the behavioral manipulation. The microdialysis probes were perfused with a constant rate of 3.33 µl/min with sterile artificial cerebrospinal fluid (ACSF; composition: 20 mM NaCl, 3.5 mM KCl, 1.1 mM KH$_2$PO$_4$, 1.3 mM MgCl$_2$, 2.5 mM CaCl$_2$, 20 mM glucose, 30 mM NaHCO$_3$, 0.4 mM ascorbate, 0.8 mM thiourea, 2 mM Na-pyruvate; pH adjusted to 7.4) for 1 h equilibration, during which no samples were collected. After equilibration, three 30-min (100 µl each) baseline samples were collected before any behavioral challenge began. Five more 30-min (100 µl each) microdialysate samples were then collected during and after a behavioral challenge. All the samples were collected in 1.5-ml low-retention Eppendorf tubes placed on ice during collection and immediately frozen after collection on dry ice for storage at −80° C.

2.2.3 The Effects of Behavioral Manipulations on OT Content in BNST$_{dl}$ Microdialysates The following behavioral manipulations were performed during BNST$_{dl}$ microdialysis: i) fear conditioning: cued fear conditioning (presentations of cue and shock, n=8) vs. contextual fear conditioning (shock only, n=6) vs. CTRL (n=9), ii) acute stress exposure: forced swimming (FS, n=8) vs. control condition (CTRL, n=10), and iii) social interaction (SI, n=6) vs. CTRL (n=8). On any experimental day, treatment groups were counterbalanced such that microdialysis samples from CTRL rats (no behavioral manipulations) were collected in the same room and time as rats exposed to behavioral manipulations. Each rat was individually housed for the duration of the microdialysis experiment.

2.2.3.1 Fear-Conditioning

All Experiments were conducted in SR-LAB startle chambers with cylindrical animal enclosures (San Diego Instruments, San Diego, Calif.), according to the protocol previously described (Moaddab and Dabrowska, 2017). During the fear conditioning, a single LED bulb positioned on the ceiling inside the startle chamber was used as the visual conditioned stimulus (CS). In addition, a grid floor made of stainless steel bars placed inside the enclosures delivered foot shocks as the unconditioned stimulus (US). The presentation and sequence of all stimuli as well as recording of the responses were automatically performed by the SR-LAB software. During habituation (day 1) rats were placed in cylindrical enclosures inside the chambers for 20 min. On the next day (pre-test, day 2), rats were placed in the same enclosures, where after a 5 min acclimation they were presented with 30 startle-eliciting white-noise bursts (WNB, 95 dB, 50 ms, inter-trial-interval 30 s). A high-frequency loudspeaker, mounted 24 cm above the enclosures, provided WNB and background white-noise (70 dB), which continuously played throughout the session. These habituation procedures were designed to reduce novelty-induced stress and to mimic the design used in the behavioral experiments below. Rats were assigned into three treatments groups based on their mean acoustic startle response (ASR). On day 3, rats underwent stereotaxic surgery for microdialysis probe implantation in the BNST$_{dl}$. They recovered for 2 days prior to fear conditioning training.

Figure 5:
FIG. 5 illustrates a schematic representation of the experimental design. (A) Rats were habituated to the chambers and tested for an acoustic startle response (ASR). $BNST_{dl}$ microdialysates were collected prior, during, and following fear conditioning. Rats were subjected to either cued fear conditioning (cue light paired with a shock, CS-US), or contextual fear conditioning (shock not signaled by a cue, US). Control rats were placed inside the microdialysis cages without a light or shock exposure. (B) Following cued or contextual fear conditioning, rats were perfused and hypothalamic sections were processed for double immunofluorescence labeling with antibodies against OT and immediate early gene expression, cFos. (C) Prior to cued fear conditioning (CS-US), cannulated rats were injected bilaterally into the $BNST_{dl}$ with OT, oxytocin receptor antagonist (OTA), or artificial cerebrospinal fluid (ACSF) in Context A. Twenty-four hours later, rats were tested for the recall of cued and non-cued fear in context B. The recall test consisted of 10 post-shock ASR trials (excluded from analysis), followed by ASR measured during presence (CS+) or absence (CS−) of cue light, mixed in a pseudorandom order. Twenty-four hours later, rats were tested for the contextual fear recall (ASR measured without CS+ presentations) in context A.
Figure 5:
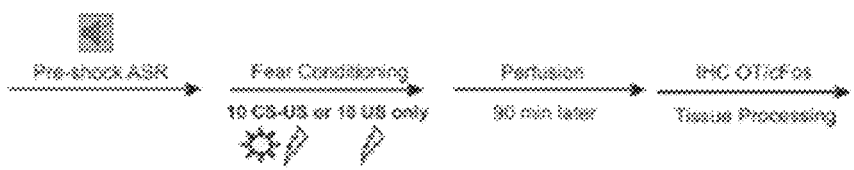
Figure 5:
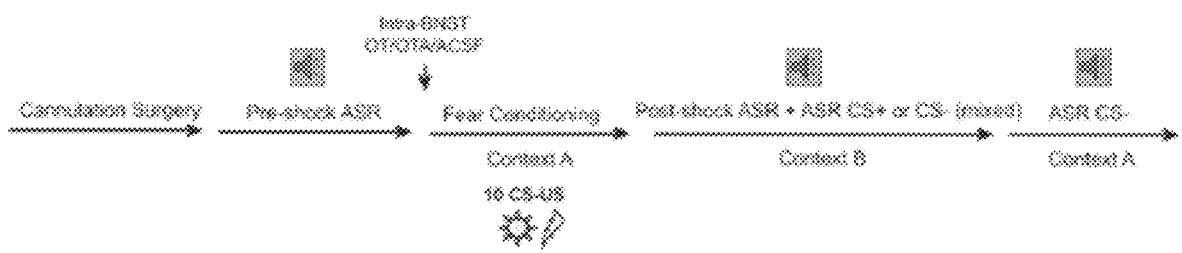

On any given experimental day, three rats were placed individually in microdialysis cages in the behavioral room with the SR-LAB apparatus. Microdialysis tubing was connected as above and three baseline microdialysate samples were collected. After baseline samples collection, two rats were transferred individually to the SR-LAB chambers inside cylindrical enclosures with grid floor conveying foot shocks. A swivel was attached to a small hook in the SR-LAB chamber ceiling to allow free animal movement inside the enclosures. Fear conditioning session began in parallel with microdialysis sample collection. After 5 minutes of acclimation, one experimental rat received 10 presentations of a 3.7 s cue light (conditioned stimulus, CS), each co-terminating with a 0.5 s foot shock (unconditioned stimulus, US; 0.5 mA, inter-trial-interval 60-180 s). Another rat placed in a neighboring chamber received the same 10 foot shocks without the cue light presentation. After a 5 min acclimation period, the fear conditioning session continued for 20 more minutes, and the rats remained inside the chambers for additional 5 minutes after the session ended, after which the microdialysate sample was collected (100 µl). The rats were then returned to their microdialysis cages and 4 more samples were collected in 30-min intervals. Samples from the third control rat, placed in a Plexiglas cage, were continuously collected in the same room see FIG. 5 (A).

2.2.3.2 Forced-Swimming (FS)

Rats were individually placed in Plexiglas cages and three baseline samples were collected. Next, rats were placed in Plexiglas tanks filled with water (20° C., up to 40 cm) and forced to swim for 10 min (Dabrowska et al., 2008). Plexiglas tanks were placed near the microdialysis cages so that rats could be transferred to the tank filled with water without disconnecting the spiral tubing. The swivel arm with spiral tubing was attached to a trim of Plexiglas tank for the duration of the FS, which allowed for tubing to stay intact and sample collection to remain undisturbed 203 during the event of rats diving inside water tanks. Hence, microdialysis samples were continuously collected during FS session. After 10 minutes, rats were removed from the tanks and placed in intermediate cages filled with paper towels for 5 minutes. They were then returned to microdialysis cages and five more microdialysis samples were collected, including the sample collected during FS session.

2.2.3.3. Social Interactions (SI)

After three baseline sample collections, a novel rat was placed in the microdialysis cage with the experimental rat for 10 minutes. Rats interacted without disconnecting the spiral tubing so that microdialysis samples were collected continuously from the experimental rat. After 10 min, the novel rat was removed and five more microdialysis samples were collected, including the sample collected during SI.

2.2.4. Probe Placement

Following microdialysis and behavioral testing, all rats were euthanized using isoflurane overdose and decapitation. Probes were perfused with Chicago Sky Blue 6B dye (Alfa Aesar, Ward Hill, Mass.) as a 2% solution in 0.9% saline. The extracted brains were sliced on an SM2000 R sliding microtome (Leica Biosystems, Nussloch, Germany) (50 µm) and photographed to confirm proper placement of the probe. Proper probe or cannula placement met the following criteria: probe tip located in the BNST$_{dl}$ (Bregma +0.10 mm to −0.36 mm), above the anterior commissure, below the lateral ventricle and medial to the internal capsule see FIG. 6.

2.2.5. Radioimmunoassay for OT

Frozen dialysates samples were evaporated until dry in a vacuum concentrator (Jouan RC10.10, Thermo Fisher Scientific) with a freeze-dry system (FreeZone 6, LABCONCO). All evaporated microdialysate samples were treated identically. The content of OT in each dialysate was quantified with a highly sensitive (0.1 pg OT/100 µl sample) and selective radioimmunoassay (RIA, minimal affinity for arginine-vasopressin, RIAgnosis, Munich, Germany), as previously described (Neumann et al., 1993; Ross et al., 2009; Bosch et al., 2016; Martinon and Dabrowska, 2018). Cross-reactivity of the polyclonal antiserum with arginine-vasopressin and other related peptides was <0.7%. Intra- and inter-assay coefficients of variation were <8% and <11%, respectively.

2.2.6 Statistical Analysis

Data are presented as mean±standard error of mean (SEM) of OT content in $BNST_{dl}$ microdialysates expressed as pg per 100 μl sample (see FIG. 7). Results were first analyzed by a within-group, one-way repeated measures analysis of variance (ANOVA) for each treatment group. Where the F-ratio was significant, all pairwise post hoc comparisons were made using Bonferroni's test by comparing the mean of each time point (post-treatment) with the mean of the three baseline samples (pre-treatment). For analysis between treatment groups, data are presented as percentage change±SEM. Here, OT content in microdialysates for each rat was expressed as percent change from its own baseline values (mean of three baseline samples, 100%) for each time point measured. Results were then analyzed by a two-way repeated measures ANOVA with the factors TIME (measured after behavioral challenge) and TREATMENT (CTRL vs. FS or CTRL vs. SI). In the FPS experiment, results were analyzed by a two-way repeated measures ANOVA with the factors TIME and TREATMENT (CTRL vs. cue and shock vs. shock only). Where the F-ratio was significant, all pairwise post hoc comparisons were made using Bonferroni's test. Statistical analyses were completed using GraphPad Prism version 6 (GraphPad Software Inc., San Diego, Calif.). P<0.05 was considered significant.

2.3 The Effect of Fear Conditioning on Activation of Hypothalamic OT Neurons Here, 15 rats were used to determine whether OT neurons in the hypothalamus are activated in response to fear conditioning. Double immunofluorescence labeling was conducted in hypothalamic sections with antibodies against OT and immediate early gene expression, cFos, following fear conditioning see FIG. 5 (A).

2.3.1 Fear-Conditioning and Timely Perfusions

Rats were habituated in SR-LAB chambers, tested for their baseline ASR as above, and assigned into three treatments groups based on their mean ASR. They were fear-conditioned the next day in SR-LAB chambers as above. One group of rats (n=5) was exposed to 10 presentations of cue light, each co-terminating with a foot shock (as above), whereas another group of rats received 10 presentations of foot shock only (n=5), as above. Control rats were placed inside the SR-LAB chambers but did not receive cue or shock presentation. 90 min following fear conditioning, rats were transcardially perfused with 10% buffered formalin, as described before (Dabrowska et al., 2011). Brains were then sliced (50 μm thickness) on Leica microtome (as above) and processed for immunohistochemistry see FIG. 5 (B).

2.3.2 Double Immunofluorescence

Every 3rd brain section from the entire hypothalamus (Bregma −0.60 mm to −2.40 mm) from all 15 rats was processed for double immunofluorescence using anti-OT mouse monoclonal antibody (clone 4G11, 1:5000, MAB5296, Chemicon-Millipore, Billerica, Mass.), as described before (Dabrowska et al., 2011), and combined with anti-cFos rabbit polyclonal antibody (sc-52, 1:2000, Santa Cruz Biotechnology, Santa Cruz, Calif.). Double immunofluorescence protocol was performed as before (Dabrowska et al., 2011). Briefly, sections were rinsed in phosphate buffer saline (PBS), incubated in 270 3% normal goat serum (NGS, Thermo Fischer Scientific, Waltham, Mass.) in 0.5% Triton X-100 (Sigma-Aldrich, St. Louis, Mo.) in PBS, and incubated for 48 h at 4° C. with the above primary antibodies diluted in 0.5% Triton X-100/PBS solution. Sections were rinsed in PBS and incubated at room temperature for 2 h with specific Alexa Fluor secondary antibodies (1:500, Molecular Probes, Thermo Fischer Scientific, Waltham, Mass.): Alexa Fluor 488 goat anti-mouse IgG and Alexa Fluor 594 goat anti-rabbit IgG. Following incubation with secondary antibodies, sections were rinsed in PBS and phosphate buffer (PB), mounted on gelatin-coated glass slides and coverslipped using Mowiol-DABCO (Sigma-Aldrich, St. Louis, Mo.) media.

2.3.3 Confocal Microscopy and Cells Counting

All sections were first briefly screened using an Eclipse Ni-E upright microscope (Nikon, Melville, N.Y.) and categorized into specific Bregma levels from −0.60 mm to −2.28 mm based on the rat brain atlas (Paxinos and Watson, 2009). An FV10i confocal laser-scanning microscope (Olympus, Waltham, Mass.) was used to analyze immunofluorescence signal and to acquire high-resolution Z-stack images. Z-stacks (60× magnification at 1 μm interval) were taken bilaterally from the PVN, SON, and AN (both medial and lateral AN when applicable) of 4-6 hypothalamic brain sections from each rat (results from brain sections grouped in the rostral caudal manner are shown in FIG. 8). Quantitative analysis of double-labeled OT/cFos neurons in the PVN, SON, and AN was performed offline on acquired Z-stack images using FLUOVIEW software (Version 3.0, Olympus) for data analysis. For each Z-stack image, the cells co-localizing cFos and OT were counted and compared to total number of neurons expressing OT alone. Co-localization analysis was accomplished by switching between filters in acquired Z-stack images to confirm dual immunofluorescence in a cell observed in the same focal plane.

2.3.4 Statistical Analysis

Data are presented as mean±SEM of percentage of OT neurons co-localizing cFos in each of the hypothalamic nucleus, namely the PVN, SON, and AN. Results were first analyzed by a one-way ANOVA between three conditions (TREATMENT). In addition, due to the observed considerable variation in OT neurons' activation rostro-caudally, results from anterior to posterior hypothalamic sections were analyzed separately, grouping these sections into three AREAS (AREA 1, Bregma −0.60 mm to 1.20 mm; AREA 2, Bregma −1.32 mm to −1.72 mm; and AREA 3, Bregma −1.80 to −2.28 mm) based on rat brain atlas (Paxinos and Watson, 2009). The PVN and AN were divided into all three AREAS, whereas SON was divided into two AREAS (AREA 1 and 2). Results were analyzed by a two-way repeated measures ANOVA with factors TREATMENT and AREA. Where the main or interaction effect was significant, all pairwise post hoc comparisons were made using Bonferroni's test.

2.4 The Effects of OT or OTA Administration into the $BNST_{dl}$ on Fear Conditioning A total of 75 rats were used for FPS experiments. The ACSF-treated group consisted of 23 rats, whereas there were 14 OT and 16 OTR antagonist (OTA)-treated rats included in the main analysis. In addition, there were 10 OT and 12 OTA-treated rats excluded from the main analysis due to cannula misplacement and inability to unequivocally confirm the correct location of the cannula due to dye absence (see inclusion criteria in 2.2.4). These rats were analyzed as negative controls.

2.4.1 Guide Cannula Implantation

Stereotaxic surgery technique was identical to above except that guide cannulas were implanted bilaterally instead of a microdialysis probe (Moaddab and Dabrowska, 2017).

2.4.2. Drugs

OT acetate salt (H-2510, Bachem Inc., CA) and a selective OTA (V-905, NIMH Chemical Synthesis and Drug Supply Program) $(d(CH_2)_5^1, D\text{-}Tyr^2, Thr_4, Orn_8, des\text{-}Gly$-

NH$_{2,9}$)-vasotocin trifluoroacetate salt (Manning et al., 2012) were stored in −80 degrees Celsius freezer and diluted in sterile ACSF (composition as above, pH=7.4) before each experiment.

2.4.3 Drug Administration

OT (100 ng), OTA (200 ng), or ACSF (all in volume of 0.5 μl per side) was injected bilaterally into the BNST$_{dl}$ through a microinjector (28-gauge, 7 mm length; Plastics One, Roanoke, Va.) as described before (Moaddab and Dabrowska, 2017). Doses of OT and OTA were chosen based on previous studies on fear and anxiety in rats (Bale et al., 2001; Toth et al., 2012; Lahoud and Maroun, 2013; Neumann and Slattery, 2016; Moaddab and Dabrowska, 2017). Rats were assigned based on a second pre-test ASR into three treatment groups. Fear conditioning sessions were performed 10 min after the intra-BNST$_{dl}$ injections.

2.4.4 Fear-Conditioning and Fear Recall Testing Using FPS

FPS procedures were modified based on previous studies and according to protocol described in detail before (Walker et al., 2009; Missig et al., 2010; Ayers et al., 2011; Moaddab and Dabrowska, 2017). On days 1 and 2, rats underwent two pre-test sessions. On day 3 (fear conditioning), animals were placed in cylindrical enclosures containing a grid floor conveying foot shocks (as above). After 5 min acclimation, animals received 10 presentations of a 3.7 s cue light (CS), each co-terminating with a 0.5 s foot shock (US; 0.5 mA, inter-trial-interval 60-180 s). Background noise was absent during the conditioning session. Enclosures and chambers were cleaned with PREempt RTU disinfectant solution (Virox Technologies, Oakville, Canada) before and after each fear 337 conditioning session (context A). Twenty-four hours later, on day 4, rats were tested for FPS expression (recall test) in context B. After 5 min of acclimation, they were exposed to 50 startle-eliciting WNBs (as above) and levels of cued and non-cued fear were measured. A background white noise of 70 dB continuously played throughout the session. The session consisted of 10 baseline startle trials (excluded from the analysis) followed by an additional 40 trials, with half presented in the presence of the cue light (CS+, light-noise) and the other half without the CS (CS−, noise-alone) in a pseudorandom order (inter-trial-interval 30 s). To make context A distinct from context B, enclosures and chambers were cleaned with 70% ethanol before and after the fear conditioning sessions (different than in fear conditioning). The grid floor was also removed from the enclosures during cued FPS testing. In addition, a different experimenter from the training session performed the FPS testing session. On day 5, the same rats were tested for contextual fear recall in context A, where after 10 baseline startle trials (excluded from the analysis), startle amplitude was measured during 40 additional CS− trials (noise-alone, inter-trial-interval 30 s, FIG. 5, C).

2.4.5 Data Analysis

Startle amplitude was defined as the maximum peak voltage within the first 200 ms after onset of the WNB. Shock reactivity amplitude was recorded during the fear conditioning session and was defined as the maximum peak voltage that occurred during the 500 ms foot shock delivery. Cued, non-cued, and contextual fear, were calculated as percent change scores of startle amplitude based on previous FPS studies (Walker et al., 2009; Missig et al., 2010; Ayers et al., 2011; Moaddab and Dabrowska, 2017). Cued fear=[(light-noise trials−noise-alone trials)/noise-alone trials]×100% in context B. Non-cued fear=[(noise-alone trials−pre-shock trials)/pre-shock trials]×100% in context B. Contextual fear=[(noise-alone trials−pre-shock trials)/pre-shock trials]×100% in context A. Furthermore, to determine the ability of an individual rat to discriminate between cued (signaled) and non-cued (unsignaled) fear, the discrimination index (DI) was calculated for individual rats by dividing their percent change score of cued fear by their percent change score of non-cued fear responses according to the following formula: Discrimination Index (DI)=[(light-noise trials/noise-alone trials)/(noise-alone trials/pre-shock trials)] in context B.

2.4.6 Statistical Analysis

All data are presented as mean±SEM. For the FPS experiment, mean startle amplitude was analyzed by a two-way repeated measures ANOVA with the factors TRIAL TYPE (pre-shock, noise-alone, and light-noise) and TREATMENT (OT, OTA, and ACSF). Where the F-ratio was significant, all pairwise post hoc comparisons were made using Bonferroni's test. The percent change scores (cued fear, non-cued fear, and contextual fear) were analyzed separately for each measure using a one-way ANOVA. The effects of drug treatment on discrimination index (DI) scores and on shock reactivity during fear conditioning were analyzed by a one-way ANOVA. To determine the effect of treatment on DI scores as a function of time during the fear recall session, results were analyzed with a two-way repeated measures ANOVA with the factors TIME (recall session divided into four blocks of 10 trials, each consisting of 5 noise-alone and 5 light-noise trials) and TREATMENT (OT, OTA or ACSF). Statistical analyses were completed using GraphPad Prism version 6 (GraphPad Software Inc., San Diego, Calif.). $P<0.05$ was considered significant.

3. Results 3.1 The Effects of Behavioral Manipulations on OT Content in BNST$_{dl}$ Microdialysates OT content (pg/100 μl) in BNST$_{dl}$ microdialysates for all behavioral groups is shown in FIG. 7.

3.1.1 Cued, but not Contextual Fear Conditioning, Increases OT Content in BNST$_{dl}$ Microdialysates Baseline OT concentration in BNST$_{dl}$ microdialysates from rats included in the fear conditioning experiment had a mean±SEM of 1.15±0.03 pg. It was found that OT content did not differ between three baseline BNST$_{dl}$ microdialysates in rats exposed to contextual fear conditioning (F (1.150, 5.751)=1.977, P=0.2148, cued fear conditioning (F (1.502, 10.51)=1.740, P=0.2216), or CTRL conditions (F (1.106, 6.636)=1.331, P=0.2948), suggesting stable OT levels before behavioral manipulations. A one-way repeated measures ANOVA revealed no significant effect of treatment on OT content in BNST$_{dl}$ microdialysates in CTRL rats (F (2.502, 15.01)=0.08814, P=0.9468). Additionally, no significant within-treatment group effects were observed in rats exposed to contextual fear conditioning (F (2.597, 12.98)=0.1707, P=0.8921). However, there was a significant TREATMENT effect on OT content in BNST$_{dl}$ microdialysates in rats exposed to cued fear conditioning (F (3.010, 21.07)=3.621, P=0.0297), see FIG. 7. Percentage changes from baseline OT content were compared between treatment groups in their respective time-points after the fear conditioning. A two-way repeated measures ANOVA revealed no significant main effect of TREATMENT (F (2, 20)=1.937, P=0.1702), and no significant effect of TIME (F (5, 100)=1.153, P=0.3378). However, there was a significant interaction between TIME and TREATMENT (F (10, 100)=2.002, P=0.0408). Post hoc analysis with Bonferroni's multiple comparison test revealed a significantly greater percentage change of OT content in BNST$_{dl}$ microdialysates in rats exposed to cued fear conditioning (134.66%±12.95 of baseline content) at 30 min in comparison to CTRL rats (98.86%±6.56, P<0.01) and rats exposed to contextual fear conditioning (98.29%±8.04, P<0.01). No significant effects were observed at 60, 90, 120, and 150 min after the fear conditioning in any group, see FIG. 9 (A).

3.1.2 Forced-Swimming does not Affect OT Content in $BNST_{dl}$ Microdialysates

The baseline OT concentration in the $BNST_{dl}$ from rats included in FS experiment had a mean±SEM of 1.04±0.05 pg. To determine if the OT content in baseline $BNST_{dl}$ microdialysates was stable before any behavioral manipulations were introduced, OT content between three baseline microdialysates was compared for each treatment group with a one-way repeated measures ANOVA. It was found that OT content did not differ between three baseline microdialysates in rats exposed to FS (F (1.235, 8.644)=1.405, P=0.2780), or CTRL rats for FS (F (1.542, 13.88)=1.014, P=0.3680). OT concentration in $BNST_{dl}$ microdialysates was then compared within treatment groups with a one-way repeated measures ANOVA. As expected, no significant effect of treatment was observed in CTRL rats (F (2.510, 22.59)=1.220, P=0.3209). There were also no significant effects observed in rats exposed to 10 min FS (F (2.275, 15.92)=0.7365, P=0.5109), see FIG. 7. Comparing percentage change from baseline OT content across all time-points in control and FS rats with a two-way repeated measures ANOVA revealed no significant main effect of TREATMENT (F (1, 16)=1.010, P=0.3298), no significant effect of TIME (F (5, 80)=1.414, P=0.2282), and no significant interaction between TIME and TREATMENT (F (5, 80)=0.4828, P=0.7881), see FIG. 9 (B).

3.1.3 Social Interactions do not Affect OT Content in $BNST_{dl}$ Microdialysates Baseline OT concentration in $BNST_{dl}$ microdialysates from rats included in SI experiment had a mean±SEM of 1.04±0.03 pg. It was found that OT content did not differ between baseline $BNST_{dl}$ microdialysates in rats exposed to SI (F (1.115, 5.573)=2.160, P=0.1977), or CTRL rats for SI (F (1.564, 9.383)=1.651, P=0.2403). A one-way repeated measures ANOVA revealed no significant effect of treatment on OT content in $BNST_{dl}$ microdialysates in CTRL rats (F (2.260, 15.82)=1.332, P=0.2949). There was also no significant effect observed in rats exposed to 10 min SI (F (2.371, 11.85)=1.379, P=0.2932), see FIG. 7. Comparing percentage changes from baseline OT content across all time-points in CTRL and SI rats with a two-way repeated measures ANOVA revealed no significant main effect of TREATMENT (F (1,12)=1.432, P=0.2546), no significant effect of TIME (F (5, 60)=1.394, P=0.2396), and no significant interaction between TIME and TREATMENT (F (5,60)=0.8411, P=0.5259), see FIG. 9 (C).

3.2 The Effect of Fear Conditioning on OT Neurons Activation in the Hypothalamus Results from all hypothalamic sections are shown in FIG. 8.

3.2.1 Fear Conditioning Activates OT Neurons in the PVN

First, the results from all hypothalamic sections were analyzed with one-way ANOVAs. In the PVN, there was a significant main effect of TREATMENT on the percentage of activated OT neurons in response to fear conditioning (F (2, 129)=3.142, P=0.0465). Post hoc analysis with Bonferroni's multiple comparison test revealed a significantly greater percentage of activated OT neurons in rats exposed to contextual fear conditioning (13.69%±2.73 of all counted OT neurons in the PVN) in comparison to CTRL rats (5.43%±2.11, P=0.0406). However, percentage of OT neuronal activation did not differ between rats exposed to cued fear conditioning (9.64%±2.33) compared to CTRL rats (P=0.6495). There was also no significant difference in percentage of activated OT neurons in rats exposed to contextual vs. cued fear conditioning (P=0.7511) see FIG. 10 (A-C"); FIG. 11 (A). Comparing percentage of activated OT neurons in the PVN across all rostro-caudal AREAS (1-3) for all 3 conditions with a two-way repeated measures ANOVA revealed no significant main effect of TREATMENT (F (2, 11)=0.7313, P=0.5033), no significant main effect of AREA (F (2, 22)=0.1384, P=0.8715), and no significant interaction between TREATMENT and AREA (F (4, 22)=1.145, P=0.3617, see FIG. 11 (B).

3.2.2 Fear Conditioning Causes Robust Activation of OT Neurons in the SON

In the SON, there was a significant main effect of TREATMENT on percentage of activated OT neurons in response to fear conditioning (F (2, 82)=31.40, P<0.0001). Post hoc analysis with Bonferroni's multiple comparison test revealed significant difference between percentages of OT neurons expressing cFos between all three conditions. There was a significantly greater percentage of activated OT neurons in rats exposed to contextual fear conditioning (22.03%±2.38 of all OT neurons) in comparison to CTRL rats (3.81%±0.79, P<0.0001). There was also a significantly greater percentage of activated OT neurons in rats exposed to cued fear conditioning (11.91%±1.6) compared to CTRL rats (P=0.0030). A significant difference was also observed between activated OT neurons in rats exposed to contextual vs. cued fear conditioning (P=0.0003), see FIG. 10, D-F"; FIG. 11, C. Comparing percentages of activated OT neurons across rostral to caudal AREAS for all 3 conditions with a=two-way repeated measures ANOVA revealed a significant main effect of TREATMENT (F (2,11)=11.21, P=0.0022), no significant effect of AREA (F (1, 11)=0.05418, P=0.8202), and no significant interaction between TREATMENT and AREA (F (2, 11)=1.505, P=0.2644). In AREA 1, post hoc analysis with Bonferroni's multiple comparison test revealed a significantly greater percentage of activated OT neurons in rats exposed to contextual fear conditioning (24.69%±5.09) in comparison to CTRL rats (5.60%±2.08, t (22)=3.526, P=0.0057). There was no significant difference in percentage of activated OT neurons seen in rats exposed to cued fear conditioning (10.40%±3.01) compared to CTRL rats (t (22)=0.8871, P>0.9999). However, there was a significant difference in percentage of activated OT neurons between rats exposed to contextual vs. cued fear conditioning within AREA 1 (t (22)=2.799, P=0.0314). Similarly, within AREA 2, there was a significantly greater percentage of activated OT neurons in rats exposed to contextual fear conditioning (28.12%±5.05), in comparison to CTRL rats (1.78%±0.96, t (22)=4.867, P=0.0002). There was no significant difference between percentages of activated OT neurons seen in rats exposed to cued fear conditioning (11.99%±2.84) in comparison to CTRL rats (t (22)=1.887, P=0.2174). Alternately, tests revealed a significant difference between percentages of activated OT neurons in rats exposed to contextual vs. cued fear conditioning within AREA 2 (t (22)=3.161, P=0.0136), see FIG. 11 (D).

3.2.3 Fear Conditioning Causes Robust Activation of OT Neurons in the AN

In the AN, a one-way ANOVA showed a significant main effect of TREATMENT on percentage of activated OT neurons in response to fear conditioning (F (2, 150)=12.62, P<0.0001). A post hoc analysis with Bonferroni's multiple comparison test revealed significant differences between percentages of OT neurons expressing cFos between groups, with a significantly greater percentage of activated OT neurons in rats exposed to contextual fear conditioning (18.95%±2.14) in comparison to CTRL rats (4.69±1.57, P<0.0001). There was also a significantly greater percentage of activated OT neurons in rats exposed to cued fear conditioning (13.58%±2.75) compared to CTRL rats (P=0.0168). There was no significant difference between percentages of activated OT neurons in rats exposed to contextual fear conditioning and cued fear conditioning (P=0.2564), see FIG. 10 (G-I"); FIG. 11 (E). Comparing percentages of activated OT neurons in the AN across all three AREAS for all three conditions with a two-way repeated measures ANOVA revealed no significant effect of TREATMENT (F (2, 11)=2.331, P=0.1432), a trend for the AREA (F (2, 22)=3.060, P=0.0672), and no interaction between AREA and TREATMENT F (4, 22)=1.416, P=0.2618). see FIG. 11 (F).

3.3 Effects of OT or OTA Administration into the $BNST_{dl}$ on the Acquisition of FPS 3.3.1 Acquisition of Cued Fear Conditioning All animals exhibited a significantly potentiated startle response in light-noise trials compared to noise-alone trials. There was a significant main effect of TRIAL TYPE (noise-alone, light-noise) (F (1, 50)=32.01, P<0.0001), but no main effect of TREATMENT (F (2, 50)=0.1656, P=0.8478), and no significant interaction between TRIAL TYPE and TREATMENT (F (2, 50)=0.7115, P=0.4958, two-way repeated measures ANOVA), see FIG. 12 (A). Comparison of percentage changes with one-way ANOVA revealed a trend in the TREATMENT effect on cued fear (F (2, 50)=2.433, P=0.0981, see FIG. 12 (B). As relatively high variability was observed in OT-treated rats, ACSF and OTA-treated groups were also compared using un-paired t-test, which revealed a trend in the OTA effect on cued fear (P=0.0763). Rats with injection sites outside the BNST (negative controls) also showed significantly potentiated startle response in light-noise trials compared to noise-alone trials. There was a significant main effect of TRIAL TYPE (noisealone, light-noise) (F (1, 42)=19.14, P<0.0001), but no main effect of TREATMENT (F (2, 42)=0.6302, P=0.5370). There was no significant interaction between TRIAL TYPE and TREATMENT (F (2, 42)=0.5271, P=0.5942, two-way repeated measures ANOVA). The percent change analysis revealed no significant effect of TREATMENT on cued fear (F (2, 42)=0.9392, P=0.3990).

3.3.2 Acquisition of Non-Cued Fear Conditioning

Quantitative analysis showed a significant enhancement of startle amplitude in noise-alone trials compared to pre-shock trials across all groups. There was a main effect of TRIAL TYPE (F (1, 50)=22.73, P<0.0001) but no main effect of TREATMENT (F (2, 50)=0.8546, P=0.4316) and no interaction between TRIAL TYPE and TREATMENT (F (2, 50)=0.6216, P=0.5412). Similarly, the mean percent change analysis revealed no significant differences in non-cued fear between treatment groups (F (2, 50)=0.1063, P=0.8993, one-way ANOVA) see FIG. 12 (C). The negative controls showed a significant enhancement of startle amplitude in noise-alone trials compared to pre-shock trials in all animals. There was a main effect of TRIAL TYPE (F (1, 42)=13.47, P=0.0007) but no main effect of TREATMENT (F (2, 42)=1.415, P=0.2542). There was no interaction between TRIAL TYPE and TREATMENT (F (2, 42)=0.3271, P=0.7229). The mean percent change analysis showed no differences in non-cued fear between treatment groups (F (2, 42)=0.2431, P=0.7853, one-way ANOVA).

3.3.3 Acquisition of Contextual Fear Conditioning

Quantitative analysis showed a significant enhancement of startle amplitude in the training context compared to pre-shock trials across all groups. There was a main effect of TRIAL TYPE (F (1, 46)=12.45, P=0.001) but no main effect of TREATMENT (F (2, 46)=1.35, P=0.2693), and no interaction between TRIAL TYPE and TREATMENT (F (2, 46)=1.096, P=0.3429). Similarly, the mean percent change analysis showed that contextual fear did not differ between treatment groups (F (2, 46)=0.6275, P=0.5384), see FIG. 6 (D).

3.3.4 Shock Reactivity

Figure 6:
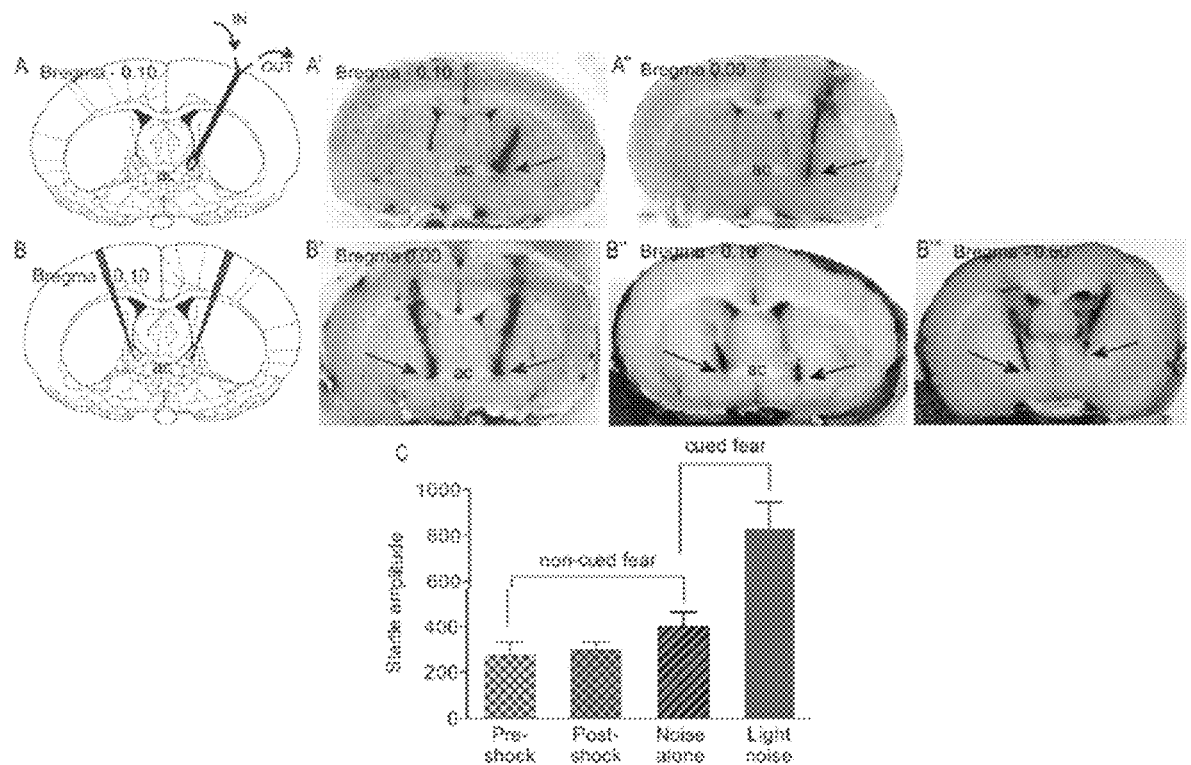
FIG. 6 illustrates representative brain sections with a unilateral track of a microdialysis probe (A-A") or bilateral cannulas (B-B''') targeting the $BNST_{dl}$. Upon completion of the experiments, the probes/cannulas were perfused with Chicago Sky Blue 6B dye. All extracted brains were sliced and all BNST sections were photographed to confirm proper placement of the probe or cannula. Examples of confirmed locations in the $BNST_{dl}$ (Bregma+0.10 mm to −0.36 mm), which met the following criteria: above the anterior commissure (ac), below the lateral ventricle and medially to the internal capsule as indicated by the arrows (included in the analysis: A' unilateral probe hit, B' bilateral cannula hit, B" unilateral cannula hit). Examples of misplaced cannula locations with probe track too lateral to the $BNST_{dl}$ as indicated by the arrow (A"), or cannula too posterior to the $BNST_{dl}$ (B''', excluded from the analysis). (C) Components of the fear potentiated startle (FPS) paradigm. Cued fear represents potentiation of the startle amplitude during presentation of the cue (CS+) in comparison to startle amplitude measured during noise alone trials. The non-cued fear represents startle potentiation during noise-alone trials (CS−) observed after the first CS+ presentation, in comparison to pre-shock startle trials.

The mean shock reactivity during the fear conditioning session was not different between ACSF, OT and OTA-treatment groups (F (2, 50)=0.1415, P=0.8684), see FIG. 6 (E).

3.3.5 Discrimination Index

The calculated total discrimination index (DI) for the FPS session was not significantly different between ACSF, OT, and OTA treatment groups (F (2, 50)=1.977, P=0.1492, one-way ANOVA), see FIG. 6 (F). This was also the case in the negative controls (F (2, 42)=0.5324, P=0.5911). However, when the DI was calculated over four time blocks, there was no significant main effect of TREATMENT (F (2, 50)=1.92, P=0.1573) or TIME (F (3, 150)=1.47, P=0.2249), but there was a significant interaction between TREATMENT and TIME (F (6, 150)=2.261, P=0.0406, two-way repeated measures ANOVA). Post hoc comparisons revealed significant differences in the discrimination indices in the fourth time block of fear memory recall between ACSF- and OT-treated groups (t (200)=2.91, P=0.0121), as well as between OT and OTA-treated groups (t (200)=3.739, P=0.0007, Bonferroni's multiple comparison test, see FIG. 13 (A). In the negative controls, the DI over four time blocks revealed no significant main effect of TREATMENT (F (2, 42)=0.5469, P=0.5828) or TIME (F (3, 126)=0.6473, P=0.5861), and there was no interaction between TREATMENT and TIME (F (6, 126)=0.2376, P=0.9634, two-way repeated measures ANOVA, see FIG. 13 (B).

While a number of example embodiments have been provided, the various aspects and embodiments disclosed herein are for purposes of illustration and are not intended to be limiting. Other embodiments can be used, and other changes can be made, without departing from the spirit and scope of the subject matter presented herein. It will be readily understood that the aspects of the disclosure, as generally described herein, and illustrated in the figures, can be arranged, substituted, combined, separated, and designed in a wide variety of different configurations, all of which are explicitly contemplated herein.

V. BIBLIOGRAPHY

Acheson D, Feifel D, de Wilde S, McKinney R, Lohr J, Risbrough V (2013) The effect of intranasal oxytocin treatment on conditioned fear extinction and recall in a healthy human sample. Psychopharmacology 229:199-208.

Ayers L, Agostini A, Schulkin J, Rosen J B (2016) Effects of oxytocin on background anxiety in rats with high or low baseline startle. Psychopharmacology 233:2165-2172.

Ayers L W, Missig Schulkin J, Rosen J B (2011) Oxytocin reduces background anxiety in a fear-potentiated startle paradigm: peripheral vs central administration. Neuropsychopharmacology: official publication of the American College of Neuropsychopharmacology 36:2488-2497.

Bale T L, Davis A M, Auger A P, Dorsa D M, McCarthy M M (2001) CNS region-specific oxytocin receptor expression: importance in regulation of anxiety and sex behavior.

The Journal of neuroscience: the official journal of the Society for Neuroscience 21:2546-2552.

Bosch O J, Kromer S A, Brunton P J, Neumann I D (2004) Release of oxytocin in the hypothalamic paraventricular nucleus, but not central amygdala or lateral septum in lactating residents and virgin intruders during maternal defence. Neuroscience 124:439-448.

Bosch O J, Dabrowska J, Modi M E, Johnson Z V, Keebaugh A C, Barrett C E, Ahern T H, Guo J, Grinevich V, Rainnie D G, Neumann I D, Young L J (2016) Oxytocin in the nucleus accumbens shell reverses CRFR2-evoked passive stress-coping after partner loss in monogamous male prairie voles. Psychoneuroendocrinology 64:66-78.

Dabrowska J, Nowak P, Brus R (2008) Reactivity of 5-HT1A receptor in adult rats after neonatal noradrenergic neurons' lesion—implications for antidepressant-like action. Brain research 1239:66-76.

Dabrowska J, Hazra R, Guo J D, Li C, Dewitt S, Xu J, Lombroso P J, Rainnie D G (2013) Striatal enriched protein tyrosine phosphatase-STEPs toward understanding chronic stress induced activation of corticotrophin releasing factor neurons in the rat bed nucleus of the stria terminalis. Biological psychiatry 74:817-826.

Dabrowska J, Hazra R, Ahern T H, Guo J D, McDonald A J, Mascagni F, Muller J F, Young L J, Rainnie D G (2011) Neuroanatomical evidence for reciprocal regulation of thecorticotrophin-releasing factor and oxytocin systems in the hypothalamus and the bed nucleus of the stria terminalis of the rat: Implications for balancing stress and affect. Psychoneuroendocrinology 36:1312-1326.

Daniel SE, Rainnie D G (2016) Stress Modulation of Opposing Circuits in the Bed Nucleus of the Stria Terminalis. Neuropsychopharmacology: official publication of the American College of Neuropsychopharmacology 41:103-125.

Davis M, Walker D L, Miles L, Grillon C (2010) Phasic vs sustained fear in rats and humans: role of the extended amygdala in fear vs anxiety. Neuropsychopharmacology: official publication of the American College of Neuropsychopharmacology 35:105-135.

De Bundel D, Zussy C, Espallergues J, Gerfen C R, Girault J A, Valjent E (2016) Dopamine D2 receptors gate generalization of conditioned threat responses through mTORC1 signaling in the extended amygdala. Molecular psychiatry 21:1545-1553.

Dumais K M, Bredewold R, Mayer T E, Veenema A H (2013) Sex differences in oxytocin receptor binding in forebrain regions: correlations with social interest in brain region- and sex specific ways. Hormones and behavior 64:693-701.

Dumais K M, Alonso A G, Immormino M A, Bredewold R, Veenema A H (2016) Involvement of the oxytocin system in the bed nucleus of the stria terminalis in the sex-specific regulation of social recognition. Psychoneuroendocrinology 64:79-88.

Duvarci S, Bauer E P, Pare D (2009) The bed nucleus of the stria terminalis mediates inter individual variations in anxiety and fear. The Journal of neuroscience: the official journal of the Society for Neuroscience 29:10357-10361.

Ebner K, Wotjak C T, 831 Landgraf R, Engelmann M (2000) A single social defeat experience selectively stimulates the release of oxytocin, but not vasopressin, within the septal brain area of male rats. Brain research 872:87-92.

Ebner K, Bosch O J, Kromer S A, Singewald N, Neumann I D (2005) Release of oxytocin in the rat central amygdala modulates stress-coping behavior and the release of excitatory amino acids. Neuropsychopharmacology: official publication of the American College of Neuropsychopharmacology 30:223-230.

Ellenbogen M A, Linnen A M, Cardoso C, Joober R (2014) Intranasal oxytocin attenuates the human acoustic startle response independent of emotional modulation. Psychophysiology 51:1169-1177.

Fani N, King T Z, Brewster R, Srivastava A, Stevens J S, Glover E M, Norrholm S D, Bradley B, Ressler K J, Jovanovic T (2015) Fear-potentiated startle during extinction is associated with white matter microstructure and functional connectivity. Cortex 64:249-259.

Gewirtz J C, McNish K A, Davis M (1998) Lesions of the bed nucleus of the stria terminalis block sensitization of the acoustic startle reflex produced by repeated stress, but not fear potentiated startle. Progress in neuro-psychopharmacology & biological psychiatry 22:625-648.

Glover E M, Phifer J E, Crain D F, Norrholm S D, Davis M, Bradley B, Ressler K J, Jovanovic T (2011) Tools for translational neuroscience: PTSD is associated with heightened fear responses using acoustic startle but not skin conductance measures. Depression and Anxiety 28(12): 1058-1066.

Goode T D, Maren S (2017) Role of the bed nucleus of the stria terminalis in aversive learning and memory. Learning & memory 24:480-491.

Grillon C, Pine D S, Lissek S, Rabin S, Bonne O, Vythilingam M (2009) Increased anxiety during anticipation of unpredictable aversive stimuli in posttraumatic stress disorder but not in generalized anxiety disorder. Biological psychiatry 66:47-53.

Gungor N Z, Pare D (2016) Functional Heterogeneity in the Bed Nucleus of the Stria Terminalis. The Journal of neuroscience: the official journal of the Society for Neuroscience 36:8038-8049.

Guzman Y F, Tronson N C, Jovasevic V, Sato K, Guedea A L, Mizukami H, Nishimori K, Radulovic J (2013) Fear-enhancing effects of septal oxytocin receptors. Nature neuroscience 16:1185-1187.

Hascup E R, of Bjerken S, Hascup K N, Pomerleau F, Huettl P, Stromberg I, Gerhardt G A (2009) Histological studies of the effects of chronic implantation of ceramic-based microelectrode arrays and microdialysis probes in rat prefrontal cortex. Brain research 1291:12-20.

Haufler D, Nagy F Z, Pare D (2013) Neuronal correlates of fear conditioning in the bed nucleus of the stria terminalis. Learning & memory (Cold Spring Harbor, N.Y.) 20:633-641.

Hitchcock J M, Davis M (1991) Efferent pathway of the amygdala involved in conditioned fear as measured with the fear-potentiated startle paradigm. Behavioral neuroscience 105:826-842.

Janeček M, Dabrowska J (2018) Oxytocin facilitates adaptive fear and attenuates anxiety responses in animal models and human studies—potential interaction with the corticotropin-releasing factor (CRF) system in the bed nucleu sof the stria terminalis (BNST). Cell and Tissue Research. https://doi.org/10.1007/x00441-018-2889-8.

Knobloch H S, Charlet A, Hoffmann L C, Eliava M, Khrulev S, Cetin A H, Osten P, Schwarz M K, Seeburg P H, Stoop R, Grinevich V (2012) Evoked axonal oxytocin release in the central amygdala attenuates fear response. Neuron 73:553-566.

Lahoud N, Maroun M (2013) Oxytocinergic manipulations in corticolimbic circuit differentially affect fear acquisition and extinction. Psychoneuroendocrinology 38:2184-2195. Landgraf R, Neumann ID (2004) Vasopressin and oxytocin release within the brain: a dynamic concept of multiple and variable modes of neuropeptide communication. Frontiers in neuroendocrinology 25:150-176.

Lange M D, Daldrup T, Remmers F, Szkudlarek H J, Lesting J, Guggenhuber S, Ruehle S, Jungling K, Seidenbecher T, Lutz B, Pape H C (2017) Cannabinoid CB1 receptors indistinct circuits of the extended amygdala determine fear responsiveness to unpredictable threat. Molecular psychiatry 22:1422-1430.

Lebow M, Neufeld-Cohen A, Kuperman Y, Tsoory M, Gil S, Chen A (2012) Susceptibility to PTSD-like behavior is mediated by corticotropin-releasing factor receptor type 2 levels in the bed nucleus of the stria terminalis. The Journal of neuroscience: the official journal of the Society for Neuroscience 32:6906-6916.

LeDoux J E, Iwata J, Cicchetti P, Reis D J (1988) Different projections of the central amygdaloid nucleus mediate autonomic and behavioral correlates of conditioned fear. The Journal of neuroscience: the official journal of the Society for Neuroscience 8:2517-2529.

Luyck K, Nuttin B, Luyten L (2017) Electrolytic post-training lesions of the bed nucleus of the stria terminalis block startle potentiation in a cued fear conditioning procedure. Brain structure & function.

Manning M, Misicka A, Olma A, Bankowski K, Stoev S, Chini B, Durroux T, Mouillac B, Corbani M, Guillon G (2012) Oxytocin and vasopressin agonists and antagonists as research tools and potential therapeutics. Journal of neuroendocrinology 24:609-628.

Marcinkiewcz C A, Mazzone C M, D'Agostino Halladay L R, Hardaway J A, DiBerto J F, Navarro M, Burnham N, Cristiano C, Dorrier C E, Tipton G J, Ramakrishnan C, Kozicz T, Deisseroth K, Thiele T E, McElligott Z A, Holmes A, Heisler L K, Kash T L (2016) Serotonin engages an anxiety and fear-promoting circuit in the extended amygdala. Nature 537:97-101.

Martinon D, Dabrowska J (2018) Corticotropin-Releasing Factor Receptors Modulate Oxytocin Release in the Dorsolateral Bed Nucleus of the Stria Terminalis (BNST) in Male Rats. Frontiers in neuroscience 12:183.

Missig G, Ayers L W, Schulkin J, Rosen J B (2010) Oxytocin reduces background anxiety in a fear-potentiated startle paradigm. Neuropsychopharmacology: official publication of the American College of Neuropsychopharmacology 35:2607-2616.

Moaddab M, Dabrowska J (2017) Oxytocin receptor neurotransmission in the dorsolateral bed nucleus of the stria terminalis facilitates the acquisition of cued fear in the fear potentiated startle paradigm in rats. Neuropharmacology 121:130-139.

Nasanbuyan N, Yoshida M, Takayanagi Y, Inutsuka A, Nishimori K, Yamanaka A, Onaka T (2018) Oxytocin-Oxytocin Receptor Systems Facilitate Social Defeat Posture in Male Mice. Endocrinology 159:763-775.

Neumann I, Russell J A, Landgraf R (1993) Oxytocin and vasopressin release within the supraoptic and paraventricular nuclei of pregnant, parturient and lactating rats: a microdialysis study. Neuroscience 53:65-75.

Neumann I D (2007) Stimuli and consequences of dendritic release of oxytocin within the brain. Biochem Soc Trans 35:1252-1257.

Neumann I D, Slattery D A (2016) Oxytocin in General Anxiety and Social Fear: A Translational Approach. Biological psychiatry 79:213-221.

Nishioka T, Anselmo-Franci J A, Li P, Callahan M F, Morris M (1998) Stress increases oxytocin release within the hypothalamic paraventricular nucleus. Brain research 781:56-60.

Paxinos Watson C, eds (2009) The rat brain in stereotaxic coordinates, Compact 6th Edition. Oxford, UK: Academic Press. Elsevier.

Pelrine E, Pasik S D, Bayat L, Goldschmiedt D, Bauer E P (2016) 5-HT2C receptors in the BNST are necessary for the enhancement of fear learning by selective serotonin reuptake inhibitors. Neurobiology of learning and memory 136:189-195.

Ravinder S, Burghardt N S, Brodsky R, Bauer E P, Chattarji S (2013) A role for the extended amygdala in the fear-enhancing effects of acute selective serotonin reuptake inhibitor treatment. Translational psychiatry 3:e209.

Ring R H, Malberg J E, Potestio L, Ping J, Boikess S, Luo B, Schechter L E, Rizzo S, Rahman Z, Rosenzweig-Lipson S (2006) Anxiolytic-like activity of oxytocin in male mice: behavioral and autonomic evidence, therapeutic implications. Psychopharmacology 185:218-225.

Robinson D A, Wei F, Wang G D, Li P, Kim S J, Vogt S K, Muglia L J, Zhuo M (2002) Oxytocin mediates stress-induced analgesia in adult mice. The Journal of physiology 540:593-606.

Ross H E, Cole C D, Smith Y, Neumann I D, Landgraf R, Murphy A Z, Young L J (2009) Characterization of the oxytocin system regulating affiliative behavior in female prairie voles. Neuroscience 162:892-903.

Sullivan G M, Apergis J, Bush D E, Johnson L R, Hou M, Ledoux J E (2004) Lesions in the bed nucleus of the stria terminalis disrupt corticosterone and freezing responses elicited by a contextual but not by a specific cue-conditioned fear stimulus. Neuroscience 128:7-14.

Toth I, Neumann I D, Slattery D A (2012) Central administration of oxytocin receptor ligands affects cued fear extinction in rats and mice in a timepoint-dependent manner. Psychopharmacology 223:149-158.

Tribollet E, Dubois-Dauphin M, Dreifuss J J, Barberis C, Jard S (1992) Oxytocin receptors in the central nervous system. Distribution, development, and species differences. Annals of the New York Academy of Sciences 652:29-38.

Veinante P, Freund-Mercier M J (1997) Distribution of oxytocin- and vasopressin-binding sites in the rat extended amygdala: a histoautoradiographic study. The Journal of comparative neurology 383:305-325.

Walker D, Yang Y, Ratti E, Corsi M, Trist D, Davis M (2009) Differential effects of the CRF-R1 antagonist GSK876008 on fear-potentiated, light- and CRF-enhanced startle suggest preferential involvement in sustained vs phasic threat responses Neuropsychopharmacology: official publication of the American College of Neuropsychopharmacology 34:1533-1542.

Walker D L, Davis M (2002) The role of amygdala glutamate receptors in fear learning, fear potentiated startle, and extinction. Pharmacology, biochemistry, and behavior 71:379-392.

Wilensky A E, Schafe G E, Kristensen M P, LeDoux J E (2006) Rethinking the fear circuit: the central nucleus of the amygdala is required for the acquisition, consolidation, and expression of Pavlovian fear conditioning. The Journal of neuroscience: the official journal of the Society for Neuroscience 26:12387-12396.

Wotjak C T, Naruo T, Muraoka S, Simchen R, Landgraf R, Engelmann M (2001) Forced swimming stimulates the expression of vasopressin and oxytocin in magnocellular neurons of the rat hypothalamic paraventricular nucleus. The European journal of neuroscience 13:2273-2281.

Zhu L, Onaka T (2002) Involvement of medullary A2 noradrenergic neurons in the activation of oxytocin neurons after conditioned fear stimuli. The European journal of neuroscience 16:2186-2198.

What is claimed is:

1. A method comprising:
a) determining a cued fear response value of a subject and a non-cued fear response value of the subject, the determining comprising the steps of:
   (i) presenting the subject with a first plurality of startling noises;
   (ii) during the presentation of each first startling noise of the first plurality of startling noises, measuring a corresponding baseline startle amplitude of the subject;
   (iii) presenting the subject with a first plurality of cues, wherein each cue of the first plurality of cues co-terminates with an aversive stimulus;
   (iv) after presenting the subject with the first plurality of cues co-terminating with the aversive stimulus, presenting the subject with a second plurality of startling noises;
   (v) after presenting the subject with a second plurality of startling noises, presenting the subject with a third plurality of startling noises arranged in a pseudo-randomly mixed order wherein a half of the third plurality of startling noises coincides with a presentation of the cue and a remaining half of the third plurality of startling noises are each presented alone, wherein each third startling noise of the third plurality of starling noises is emitted 30 seconds after a previous third startling noise of the third plurality of startling noises;
   (vi) during the presentation of each third startling noise in the half of the third plurality of startling noises coinciding with the presentation of the cue, measuring a corresponding first startle amplitude of the subject;
   (vii) during the presentation of each third startling noise in the remaining half of the third plurality of startling noises presented alone, measuring a corresponding second startle amplitude of the subject;
   (viii) averaging the measured baseline startle amplitudes of step (ii) to create a baseline startle amplitude value;
   (ix) averaging the measured first startle amplitudes of step (vi) to create a first startle amplitude value;
   (x) averaging the measured second startle amplitudes of step (vii) to create a second startle amplitude value;
   (xi) determining a cued fear response value by the formula (first startle amplitude value/second startle amplitude value)×100; and (xii) determining a non-cued fear response value by the formula (second startle amplitude value/baseline startle amplitude value)×100;

b) determining a discrimination index, wherein the discrimination index is equal to a ratio of the cued fear response value to the non-cued fear response value;
c) performing a diagnostic process comprising:
   diagnosing a presence of or susceptibility to a stress-induced psychiatric disorder if the discrimination index is less than 1 or equal to 1; or
   diagnosing an absence of or resilience to a stress-induced psychiatric disorder if the discrimination index is greater than 1; and
d) administering a therapy to the subject if diagnosed for the presence of or susceptibility to a stress-induced psychiatric disorder, wherein the therapy comprises a pharmaceutical agent or an evidence-based psychotherapy and wherein the pharmaceutical agent comprises oxytocin.

2. The method of claim 1, wherein measuring the baseline startle amplitudes occurs within 200 ms of presenting the subject with each first startling noise of the first plurality of startling noises.

3. The method of claim 1, wherein measuring the first startle amplitude occurs within 200 ms of presenting the subject with each third startling noise in the half of the third plurality of startling noises coinciding with the presentation of the cue.

4. The method of claim 1, wherein measuring the second startle amplitude occurs within 200 ms of presenting the subject with each third startling noise in the remaining half of the third plurality of startling noises presented alone.

5. The method of claim 1, wherein presenting the subject with the first plurality of cues comprises a conditioning step.

6. The method of claim 1, wherein each cue lasts for 3.7 seconds.

7. The method of claim 1, wherein the aversive stimulus comprises a 0.5 mA shock.

8. The method of claim 1, wherein presenting the subject with a second plurality of startling noises comprises a conditioning step.

9. The method of claim 1, wherein presenting the subject with a second plurality of startling noises comprises 10 noises.

10. The method of claim 1, wherein the third plurality of startling noises comprises 40 noises.

11. The method of claim 1, wherein the stress-induced psychiatric disorder includes at least one of post-traumatic stress disorder (PTSD), panic disorder, a phobia, or generalized anxiety disorder (GAD).

12. The method of claim 1, wherein the oxytocin is administered intranasally.

* * * * *